(12) United States Patent
Fraser et al.

(10) Patent No.: US 7,838,244 B2
(45) Date of Patent: Nov. 23, 2010

(54) SET1 PROTEINS AND USES THEREOF

(75) Inventors: John David Fraser, Auckland (NZ); Ries Langley, Rockville, MD (US)

(73) Assignee: Auckland Uniservices Limited, Auckland (NZ)

( * ) Notice: Subject to any disclaimer, the term of this patent is extended or adjusted under 35 U.S.C. 154(b) by 700 days.

(21) Appl. No.: 10/594,291

(22) PCT Filed: Dec. 7, 2004

(86) PCT No.: PCT/NZ2004/000317
§ 371 (c)(1), (2), (4) Date: Jul. 18, 2007

(87) PCT Pub. No.: WO2005/090381
PCT Pub. Date: Sep. 29, 2005

(65) Prior Publication Data
US 2009/0215195 A1 Aug. 27, 2009

(30) Foreign Application Priority Data
Mar. 24, 2004 (AU) .............................. 2004901570

(51) Int. Cl.
G01N 33/53 (2006.01)
(52) U.S. Cl. .......................................... 435/7.1; 435/7.2
(58) Field of Classification Search .................. None
See application file for complete search history.

(56) References Cited

U.S. PATENT DOCUMENTS

2004/0123343 A1    6/2004  La Rosa et al.

FOREIGN PATENT DOCUMENTS

| WO | 01/79144 | 10/2001 |
| WO | WO 02/077183 A | 10/2002 |
| WO | WO 02/094868 A | 11/2002 |
| WO | WO2005/092918 | 10/2005 |

OTHER PUBLICATIONS

Nislow et al. Molecular Biology of the Cell 1997, vol. 8, p. 2421-2436.*
Langley, Ries, et al, "*The Staphylococcal Superantigen-Like Protein 7 Binds IgA and Complement C5 and Inhibits IgA-FcαRI Binding and Serum Killing of Bacteria.*" Journal of Immunology, 2005, 174:2926-2933.
Haas, Pieter-Jan, et al, "The Structure of the C5a Receptor-blocking Domain of Chemotaxs Inhibitory Protein of *Staphylococcus aureus* is Related to a Group of Immune Evasive Molecules." *J. Mol. Biol.* (2005) 353, 859-872.
Rooijakkers, Suzan H.M., et al, "Staphylococcal Innate Immune Evasion.", *TRENDS in Microbiology* vol. 13 No. 12 Dec. 2005, pp. 596-601.
Kanwar, Jagat R., et al; "β7 Integrins Contribute to Demyelinating Disease of the Central Nervous System"; Journal of Neuroimmunology (103) (2000) 146-152.
Krissansen, Geoffrey W., et al, A Pseudosymmetric Cell Adhesion Regulatory Domain in the β7 Tail of the Integrin α4β7 That Interacts With Focal Adhesion Kinase and SRC, Eur. J. Immunol. 2006. 36:2203-2214.
Yuan et al. "Cloning and sequence analysis of a novel beta 2-related integrin transcript form T lymphocytes: homology of intergrin cysteine-rich repeats to domain III of lamini B chains," Int Immunol. 1990;2(11):1097-108, Erratum in: Int Immunol. Dec. 1991;3(12);1373-4.
Yuan et al. "Molecular Cloning of the mouse Integrin beta 7 Subunit" J Biol Chem. Apr. 15, 1992;267(11):7352-8.
Arcus et al., "The Three-Dimensional Structure of a Superantigen-like Protein, SET3, from a Pathogenicity Island of the *Staphylococcus aureus* Genome", The Journal of Biological chemistry 277:32274-32281, 2002.
Baba et al, "Genome and Virulence Determinants of High Virulence Community-Acquired MRSA", The Lancet 359:1819-1827, 2002.
Fraser et al., "The Staphylococcal SETs—Superantigen Like Virulence Factors Targeting IgA and Complement Factors.", Conference Presentation, Australian Society for Immunology 2003, Perth, Western Australia, Abstract submitted Sep. 15, 2003; Conference opened Jul. 12, 2003; oral presentation delivered Oct. 12, 2003. Abstract and PowerPoint™ presentation attached.
Holden et al., "Complete Genomes of Two Clinical *Staphylococcus aureus* Strains: Evidence for the Rapid Evolution of Virulence and Drug Resistance", Proceedings of the National Academy of Sciences (USA) 101:9786-9791, 2004.
Kuroda et al., "Whole Genome Sequencing of Meticillin-Resistant *Staphylococcus aureus*", The Lancet 357:1225-1240, 2001.
Langley et al., "The Staphylococcal Superantigen-Like Protein 7 Binds IgA and Complement C5 and Inhibits IgA-FcRI Binding and Serum Killing of Bacteria", The Journal of Immunology 174:2926-2933, 2005.
Williams et al., "Identification of a Novel Gene Cluster Encoding Staphylococcal Exotoxin-Like Proteins: Characterization of the Prototypic Gene and Its Protein Product, SET1", Infection and Immunity 68:4407-4415, 2002.
TrEMBLE Accession No. Q8NY48. Set22 protein. Oct. 1, 2002. Baba et al., (94% identical (Blastp) to Applicant's Seq ID 6).

* cited by examiner

Primary Examiner—Jacob Cheu
(74) Attorney, Agent, or Firm—Occhiuti Rohlicek & Tsao LLP

(57) ABSTRACT

The invention relates to methods of use of SET1 proteins or functional equivalents thereof. More particularly the invention relates to the use of SET1 proteins or functional equivalents thereof in procedure, for identification and/or isolation of IgA and the scrum complement factor C5.

33 Claims, 10 Drawing Sheets

Figure 1:
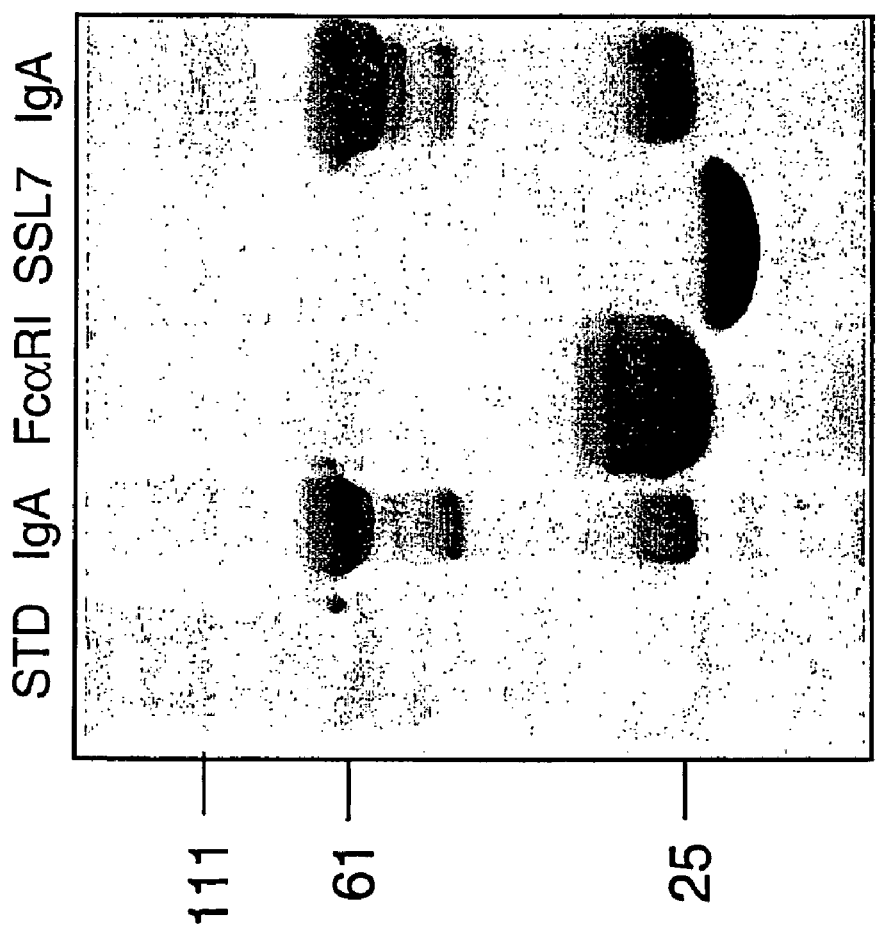

A.

```
SSL7_GL10      KEKQERVQHLYDIKDLHRYYSSESFDFSNISGKVENYNGSNVVRFNQDGQNHQLFLLGED
SSL7_GL1       KEKQERVQHLYDIKDLHRYYSSESFEFSNISGKVENYNGSNVVRFNQEKQNHQLFLLGED
SSL7_MW2       KEKQERVQHLYDIKDLHRYYSSESFEFSNISGKVENYNGSNVVRFNQENQNHQLFLSGKD
SSL7_NCTC8325  KEKQERVQHLYDIKDLHRYYSSESFEFSNISGKVENYNGSNVVRFNQENQNHQLFLLGKD
SSL7_Mu50      KEKQERVQHLYDIKDLYRYYSSESFEFSNISGKVENYNGSNVVRFNQEKQNHQLFLLGKD
SSL7_N315      KEKQERVQHLYDIKDLYRYYSSESFEFSNISGKVENYNGSNVVRFNQEKQNHQLFLLGKD
SSL7_NCTC6571  AEKQERVQHLHDIRDLHRYYSSESFEYSNVSGKVENYNGSNVVRFNPKDQNHQLFLLGKD
               *********:**:******:;**:********************  ******  *:*

SSL7_GL10      KAKYKQGLEGQNVFVVKELIDPNGRLSTVGGVTKKNNQSSETNTPLFVKKVYGGNLDASI
SSL7_GL1       KAKYKQGLQGQDVFVVKELIDPNGRLSTVGGVTKKNNQSSETNIHLLVNKLDGGNLDATN
SSL7_MW2       KDKYKEGLEGQNVFVVKELIDPNGRLSTVGGVTKKNNQSSETNTPLFIKKVYGGNLDASI
SSL7_NCTC8325  KEKYKEGIEGKDVFVVKELIDPNGRLSTVGGVTKKNNKSSETNTHLFVNKVYGGNLDASI
SSL7_Mu50      KDKYKKGLEGQNVFVVKELIDPNGRLSTVGGVTKKNNKSSETNTHLFVNKVYGGNLDASI
SSL7_N315      KDKYKKGLEGQNVFVVKELIDPNGRLSTVGGVTKKNNKSSETNTHLFVNKVYGGNLDASI
SSL7_NCTC6571  KEQYKEGLQGQNVFVVQELIDPNGRLSTVGGVTKKNNKTSETNTPLFVNKVNGEDLDASI
               *  :**:*:*:*::****:*****************:**** *::*: * :***:

SSL7_GL10      ESFSINKEEVSLKELDFKIRQHLVKNYGLYKGTTKYGKITFNLKDGEKKEIDLGDKLQFE
SSL7_GL1       DSFLINKEEVSLKELDFKIRKQLVEKYGLYQGTSKYGKITIILNGGKKQEIDLGDKLQFE
SSL7_MW2       ESFLINKEEVSLKELDFKIRQHLVKNYGLYKGTTKYGKITFNLKDGEKQEIDLGDKLQFE
SSL7_NCTC8325  DSFSINKEEVSLKELDFKIRQHLVKNYGLYKGTTKYGKITINLKDGEKQEIDLGDKLQFE
SSL7_Mu50      DSFLINKEEVSLKELDFKIRKQLVEKYGLYKGTTKYGKITINLKDBKKEVIDLGDKLQFE
SSL7_N315      DSFLINKEEVSLKELDFKIRKQLVEKYGLYKGTTKYGKITINLKDBKKEVIDLGDKLQFE
SSL7_NCTC6571  DSFLIQKEEISLKELDFKIRQQLVNNYGLYKGTSKYGKIIINLKDENKVEIDLGDKLQFE
               :** *:****:***********::**::****:*****   *:   :*  **********

SSL7_GL10      HMGDVLNSKDIQNIAVTLKQI
SSL7_GL1       RMGDVLNSKDINKIEVTLKQI
SSL7_MW2       HMGDVLNSKDIQNIAVTINQI
SSL7_NCTC8325  RMGDVLNSKDINKIEVTLKQI
SSL7_Mu50      RMGDVLNSKDIQNIAVTINQI
SSL7_N315      RMGDVLNSKDIQNIAVTINQI
SSL7_NCTC6571  RMGDVLNSKDIRGISVTINQI
               :********** *  **:;**
```

B.

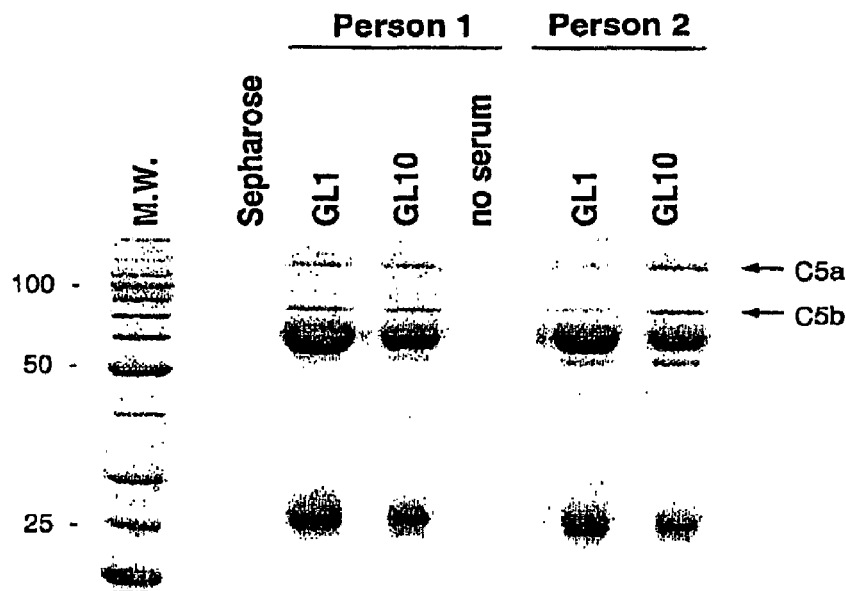

Figure 5

SEQUENCE LISTING

```
<160> NUMBER OF SEQ ID NOS: 18

<210> SEQ ID NO 1
<211> LENGTH: 231
<212> TYPE: PRT
<213> ORGANISM: Staphylococcus aureus

<400> SEQUENCE: 1

Met Lys Leu Lys Thr Leu Ala Lys Ala Thr Leu Ala Leu Gly Leu Leu
1               5                   10                  15

Thr Thr Gly Val Ile Thr Ser Glu Gly Gln Ala Val Gln Ala Ala Glu
            20                  25                  30

Lys Gln Glu Arg Val Gln His Leu His Asp Ile Arg Asp Leu His Arg
        35                  40                  45

Tyr Tyr Ser Ser Glu Ser Phe Glu Tyr Ser Asn Val Ser Gly Lys Val
    50                  55                  60
```

Glu Asn Tyr Asn Gly Ser Asn Val Val Arg Phe Asn Pro Lys Asp Gln
65                  70                  75                  80

Asn His Gln Leu Phe Leu Leu Gly Lys Asp Lys Glu Gln Tyr Lys Glu
                85                  90                  95

Gly Leu Gln Gly Gln Asn Val Phe Val Val Gln Glu Leu Ile Asp Pro
            100                 105                 110

Asn Gly Arg Leu Ser Thr Val Gly Gly Val Thr Lys Lys Asn Asn Lys
                115                 120                 125

Thr Ser Glu Thr Asn Thr Pro Leu Phe Val Asn Lys Val Asn Gly Glu
130                 135                 140

Asp Leu Asp Ala Ser Ile Asp Ser Phe Leu Ile Gln Lys Glu Glu Ile
145                 150                 155                 160

Ser Leu Lys Glu Leu Asp Phe Lys Ile Arg Gln Gln Leu Val Asn Asn
                165                 170                 175

Tyr Gly Leu Tyr Lys Gly Thr Ser Lys Tyr Gly Lys Ile Ile Ile Asn
            180                 185                 190

Leu Lys Asp Glu Asn Lys Val Glu Ile Asp Leu Gly Asp Lys Leu Gln
                195                 200                 205

Phe Glu Arg Met Gly Asp Val Leu Asn Ser Lys Asp Ile Arg Gly Ile
210                 215                 220

Ser Val Thr Ile Asn Gln Ile
225                 230

<210> SEQ ID NO 2
<211> LENGTH: 231
<212> TYPE: PRT
<213> ORGANISM: Staphylococcus aureus

<400> SEQUENCE: 2

Met Lys Leu Lys Thr Leu Ala Lys Ala Thr Leu Ala Leu Gly Leu Leu
1               5                   10                  15

Thr Thr Gly Val Ile Thr Ser Glu Gly Gln Ala Val Gln Ala Ala Glu
                20                  25                  30

Lys Gln Glu Arg Val Gln His Leu His Asp Ile Arg Asp Leu His Arg
            35                  40                  45

Tyr Tyr Ser Ser Glu Ser Phe Glu Tyr Ser Asn Val Ser Gly Lys Val
        50                  55                  60

Glu Asn Tyr Asn Gly Ser Asn Val Val Arg Phe Asn Pro Lys Asp Gln
65                  70                  75                  80

Asn His Gln Leu Phe Leu Leu Gly Lys Asp Lys Glu Gln Tyr Lys Glu
                85                  90                  95

Gly Leu Gln Gly Gln Asn Val Phe Val Val Gln Glu Leu Ile Asp Pro
            100                 105                 110

Asn Gly Arg Leu Ser Thr Val Gly Gly Val Thr Lys Lys Asn Asn Lys
                115                 120                 125

Thr Ser Glu Thr Asn Thr Pro Leu Phe Val Asn Lys Val Asn Gly Glu
130                 135                 140

Asp Leu Asp Ala Ser Ile Asp Ser Phe Leu Ile Gln Lys Glu Glu Ile
145                 150                 155                 160

Ser Leu Lys Glu Leu Asp Phe Lys Ile Arg Gln Gln Leu Val Asn Asn
                165                 170                 175

Tyr Gly Leu Tyr Lys Gly Thr Ser Lys Tyr Gly Lys Ile Ile Ile Asn
            180                 185                 190

Leu Lys Asp Glu Asn Lys Val Glu Ile Asp Leu Gly Asp Lys Leu Gln

```
                195                 200                 205
Phe Glu Arg Met Gly Asp Val Leu Asn Ser Lys Asp Ile Arg Gly Ile
    210                 215                 220

Ser Val Thr Ile Asn Gln Ile
225                 230

<210> SEQ ID NO 3
<211> LENGTH: 231
<212> TYPE: PRT
<213> ORGANISM: Staphylococcus aureus

<400> SEQUENCE: 3

Met Lys Leu Lys Thr Leu Ala Lys Ala Thr Leu Ala Leu Gly Leu Leu
1               5                   10                  15

Thr Thr Gly Val Ile Thr Ser Glu Gly Gln Ala Val His Ala Lys Glu
            20                  25                  30

Lys Gln Glu Arg Val Gln His Leu Tyr Asp Ile Lys Asp Leu Tyr Arg
        35                  40                  45

Tyr Tyr Ser Ser Glu Ser Phe Glu Phe Ser Asn Ile Ser Gly Lys Val
    50                  55                  60

Glu Asn Tyr Asn Gly Ser Asn Val Val Arg Phe Asn Gln Glu Lys Gln
65                  70                  75                  80

Asn His Gln Leu Phe Leu Leu Gly Lys Asp Lys Asp Lys Tyr Lys Lys
                85                  90                  95

Gly Leu Glu Gly Gln Asn Val Phe Val Val Lys Glu Leu Ile Asp Pro
            100                 105                 110

Asn Gly Arg Leu Ser Thr Val Gly Gly Val Thr Lys Lys Asn Asn Lys
        115                 120                 125

Ser Ser Glu Thr Asn Thr His Leu Phe Val Asn Lys Val Tyr Gly Gly
    130                 135                 140

Asn Leu Asp Ala Ser Ile Asp Ser Phe Leu Ile Asn Lys Glu Glu Val
145                 150                 155                 160

Ser Leu Lys Glu Leu Asp Phe Lys Ile Arg Lys Gln Leu Val Glu Lys
                165                 170                 175

Tyr Gly Leu Tyr Lys Gly Thr Thr Lys Tyr Gly Lys Ile Thr Ile Asn
            180                 185                 190

Leu Lys Asp Glu Lys Lys Glu Val Ile Asp Leu Gly Asp Lys Leu Gln
        195                 200                 205

Phe Glu Arg Met Gly Asp Val Leu Asn Ser Lys Asp Ile Gln Asn Ile
    210                 215                 220

Ala Val Thr Ile Asn Gln Ile
225                 230

<210> SEQ ID NO 4
<211> LENGTH: 231
<212> TYPE: PRT
<213> ORGANISM: Staphylococcus aureus

<400> SEQUENCE: 4

Met Lys Leu Lys Thr Leu Ala Lys Ala Thr Leu Ala Leu Gly Leu Leu
1               5                   10                  15

Thr Thr Gly Val Ile Thr Ser Glu Gly Gln Ala Val His Ala Lys Glu
            20                  25                  30

Lys Gln Glu Arg Val Gln Glu Leu Tyr Asp Ile Lys Asp Leu Tyr Arg
        35                  40                  45

Tyr Tyr Ser Ser Glu Ser Phe Glu Phe Ser Asn Ile Ser Gly Lys Val
```

```
                  50                  55                  60
Glu Asn Tyr Asn Gly Ser Asn Val Val Arg Phe Asn Gln Glu Lys Gln
 65                  70                  75                  80

Asn His Gln Leu Phe Leu Leu Gly Lys Asp Lys Asp Lys Tyr Lys Lys
                 85                  90                  95

Gly Leu Glu Gly Gln Asn Val Phe Val Val Lys Glu Leu Ile Asp Pro
                100                 105                 110

Asn Gly Arg Leu Ser Thr Val Gly Gly Val Thr Lys Lys Asn Asn Lys
                115                 120                 125

Ser Ser Glu Thr Asn Thr His Leu Phe Val Asn Lys Val Tyr Gly Gly
130                 135                 140

Asn Leu Asp Ala Ser Ile Asp Ser Phe Leu Ile Asn Lys Glu Glu Val
145                 150                 155                 160

Ser Leu Lys Glu Leu Asp Phe Lys Ile Arg Lys Gln Leu Val Glu Lys
                165                 170                 175

Tyr Gly Leu Tyr Lys Gly Thr Thr Lys Tyr Gly Lys Ile Thr Ile Asn
                180                 185                 190

Leu Lys Asp Glu Lys Lys Glu Val Ile Asp Leu Gly Asp Lys Leu Gln
                195                 200                 205

Phe Glu Arg Met Gly Asp Val Leu Asn Ser Lys Asp Ile Gln Asn Ile
            210                 215                 220

Ala Val Thr Ile Asn Gln Ile
225                 230

<210> SEQ ID NO 5
<211> LENGTH: 231
<212> TYPE: PRT
<213> ORGANISM: Staphylococcus aureus

<400> SEQUENCE: 5

Met Lys Leu Lys Thr Leu Ala Lys Ala Thr Leu Ala Leu Gly Leu Leu
 1               5                  10                  15

Thr Thr Gly Val Ile Thr Ser Glu Gly Gln Ala Val Gln Ala Lys Glu
                20                  25                  30

Lys Gln Glu Arg Val Gln His Leu Tyr Asp Ile Lys Asp Leu His Arg
             35                  40                  45

Tyr Tyr Ser Ser Glu Ser Phe Glu Phe Ser Asn Ile Ser Gly Lys Val
         50                  55                  60

Glu Asn Tyr Asn Gly Ser Asn Val Val Arg Phe Asn Gln Glu Asn Gln
 65                  70                  75                  80

Asn His Gln Leu Phe Leu Ser Gly Lys Asp Lys Asp Lys Tyr Lys Glu
                 85                  90                  95

Gly Leu Glu Gly Gln Asn Val Phe Val Val Lys Glu Leu Ile Asp Pro
                100                 105                 110

Asn Gly Arg Leu Ser Thr Val Gly Gly Val Thr Lys Lys Asn Asn Gln
                115                 120                 125

Ser Ser Glu Thr Asn Thr Pro Leu Phe Ile Lys Val Tyr Gly Gly
130                 135                 140

Asn Leu Asp Ala Ser Ile Glu Ser Phe Leu Ile Asn Lys Glu Glu Val
145                 150                 155                 160

Ser Leu Lys Glu Leu Asp Phe Lys Ile Arg Gln His Leu Val Lys Asn
                165                 170                 175

Tyr Gly Leu Tyr Lys Gly Thr Thr Lys Tyr Gly Lys Ile Thr Phe Asn
                180                 185                 190
```

Leu Lys Asp Gly Glu Lys Gln Glu Ile Asp Leu Gly Asp Lys Leu Gln
        195                 200                 205

Phe Glu His Met Gly Asp Val Leu Asn Ser Lys Asp Ile Gln Asn Ile
        210                 215                 220

Ala Val Thr Ile Asn Gln Ile
225                 230

<210> SEQ ID NO 6
<211> LENGTH: 201
<212> TYPE: PRT
<213> ORGANISM: Staphylococcus aureus

<400> SEQUENCE: 6

Lys Glu Lys Gln Glu Arg Val Gln His Leu Tyr Asp Ile Lys Asp Leu
1               5                   10                  15

His Arg Tyr Tyr Ser Ser Glu Ser Phe Asp Phe Ser Asn Ile Ser Gly
            20                  25                  30

Lys Val Glu Asn Tyr Asn Gly Ser Asn Val Val Arg Phe Asn Gln Asp
        35                  40                  45

Gly Gln Asn His Gln Leu Phe Leu Leu Gly Glu Asp Lys Ala Lys Tyr
    50                  55                  60

Lys Gln Gly Leu Glu Gly Gln Asn Val Phe Val Val Lys Glu Leu Ile
65                  70                  75                  80

Asp Pro Asn Gly Arg Leu Ser Thr Val Gly Val Thr Lys Lys Asn
            85                  90                  95

Asn Gln Ser Ser Glu Thr Asn Thr Pro Leu Phe Val Lys Val Tyr
        100                 105                 110

Gly Gly Asn Leu Asp Ala Ser Ile Glu Ser Phe Ser Ile Asn Lys Glu
            115                 120                 125

Glu Val Ser Leu Lys Glu Leu Asp Phe Lys Ile Arg Gln His Leu Val
    130                 135                 140

Lys Asn Tyr Gly Leu Tyr Lys Gly Thr Thr Lys Tyr Gly Lys Ile Thr
145                 150                 155                 160

Phe Asn Leu Lys Asp Gly Glu Lys Lys Glu Ile Asp Leu Gly Asp Lys
                165                 170                 175

Leu Gln Phe Glu His Met Gly Asp Val Leu Asn Ser Lys Asp Ile Gln
            180                 185                 190

Asn Ile Ala Val Thr Leu Lys Gln Ile
            195                 200

<210> SEQ ID NO 7
<211> LENGTH: 201
<212> TYPE: PRT
<213> ORGANISM: Staphylococcus aureus

<400> SEQUENCE: 7

Lys Glu Lys Gln Glu Arg Val Gln His Leu Tyr Asp Ile Lys Asp Leu
1               5                   10                  15

His Arg Tyr Tyr Ser Ser Glu Ser Phe Glu Phe Ser Asn Ile Ser Gly
            20                  25                  30

Lys Val Glu Asn Tyr Asn Gly Ser Asn Val Val Arg Phe Asn Gln Glu
        35                  40                  45

Lys Gln Asn His Gln Leu Phe Leu Leu Gly Glu Asp Lys Ala Lys Tyr
    50                  55                  60

Lys Gln Gly Leu Gln Gly Gln Asp Val Phe Val Val Lys Glu Leu Ile
65                  70                  75                  80

```
Asp Pro Asn Gly Arg Leu Ser Thr Val Gly Gly Val Thr Lys Lys Asn
                85                  90                  95
Asn Gln Ser Ser Glu Thr Asn Ile His Leu Leu Val Asn Lys Leu Asp
            100                 105                 110
Gly Gly Asn Leu Asp Ala Thr Asn Asp Ser Phe Leu Ile Asn Lys Glu
        115                 120                 125
Glu Val Ser Leu Lys Glu Leu Asp Phe Lys Ile Arg Lys Gln Leu Val
    130                 135                 140
Glu Lys Tyr Gly Leu Tyr Gln Gly Thr Ser Lys Tyr Gly Lys Ile Thr
145                 150                 155                 160
Ile Ile Leu Asn Gly Gly Lys Lys Gln Glu Ile Asp Leu Gly Asp Lys
                165                 170                 175
Leu Gln Phe Glu Arg Met Gly Asp Val Leu Asn Ser Lys Asp Ile Asn
            180                 185                 190
Lys Ile Glu Val Thr Leu Lys Gln Ile
        195                 200

<210> SEQ ID NO 8
<211> LENGTH: 696
<212> TYPE: DNA
<213> ORGANISM: Staphylococcus aureus

<400> SEQUENCE: 8
atgaaattaa aaacgttagc taaagcaaca ttagcattag gtttattaac tactggtgtc      60
attacatcag aaggtcaagc agttcaagcg gcagaaaaac aagagagagt acaacattta     120
catgatatta gagatttaca tcgatactac tcatcagaaa gtttcgaata tagtaatgtt     180
agtggtaagg ttgaaaacta caatggttct aacgttgtac gctttaaccc aaaagatcaa     240
aatcaccaat tattcttatt aggaaaagat aagaacaat ataagaagg tctacaaggc      300 caaaatgtct ttgtagtaca agaattaatt gatccaaacg gcagactatc tactgttggt     360
ggtgtaacga agaaaaacaa caaaacttct gaaactaata cacctttatt tgttaataaa     420
gttaatggtg aagatttaga tgcatcaatt gactcatttt taatccaaaa agaagaaatc     480
tcattaaaag agcttgattt caaaattaga caacaattag ttaataatta cggattatat     540
aaaggtacat ctaaatacgg taaaatcatt atcaatttga agacgaaaaa taagtagaa     600 attgatttag gtgataaatt acaattcgag cgcatgggcg atgtgttgaa tagtaaagac     660
attagaggta tatcagtcac tattaaccaa atttaa                              696

<210> SEQ ID NO 9
<211> LENGTH: 696
<212> TYPE: DNA
<213> ORGANISM: Staphylococcus aureus

<400> SEQUENCE: 9
atgaaattaa aaacgttagc taaagcaaca ttggcattag gcttattaac tactggtgtg      60
attacatcag aaggccaagc agtccacgca aagaaaaagc aagagagagt acaacattta     120
tatgatatta agacttata tcgatactac tcatcagaaa gttttgaatt cagtaatatt     180
agtggtaagg ttgaaaacta caacggttct aacgttgtac gctttaacca agaaaaacaa     240
aatcaccaat tattcttatt aggaaaagat aagataaat ataaaaaagg ccttgaaggc      300
cagaatgtct ttgtggtaaa agaattaatt gatccaaacg gtagactatc tactgttggt     360
ggtgtgacta agaaaaataa caaatcttct gaaactaata cacatttatt tgttaataaa     420
gtgtatggcg aaatttaga tgcatcaatt gactcatttt taattaataa agaagaagtt     480
```

```
tcactgaaag aacttgattt caaaattaga aagcaattag ttgaaaaata tggtttatat        540
aaaggtacga ctaaatacgg taagatcact atcaatttga aagacgagaa aaaggaagta        600
attgatttag gtgataaact gcaattcgag cgcatgggtg atgtgttgaa tagtaaggat        660
attcaaaata tagcagtgac tattaatcaa atttaa                                  696

<210> SEQ ID NO 10
<211> LENGTH: 696
<212> TYPE: DNA
<213> ORGANISM: Staphylococcus aureus

<400> SEQUENCE: 10
atgaaattaa aaacgttagc taaagcaaca ttggcattag cttattaaac tactggtgtg         60
attacatcag aaggccaagc agtccacgca aaagaaaagc aagagagagt acaacattta        120
tatgatatta aagacttata tcgatactac tcatcagaaa gttttgaatt cagtaatatt        180
agtggtaagg ttgaaaacta taacggttct aacgttgtac gctttaacca agaaaaacaa        240
aatcaccaat tattcttatt aggaaaagat aaagataaat ataaaaaagg ccttgaaggc        300
cagaatgtct ttgtggtaaa agaattaatt gatccaaacg gtagactatc tactgttggt        360
ggtgtgacta gaaaaaataa caaatcttct gaaactaata cacatttatt tgttaataaa        420
gtgtatggcg gaaatttaga tgcatcaatt gactcatttt taattaataa agaagaagtt        480
tcactgaaag aacttgattt caaaattaga aagcaattag ttgaaaaata tggtttatat        540
aaaggtacga ctaaatacgg taagatcact atcaatttga aagacgagaa aaaggaagta        600
attgatttag gtgataaact gcaattcgag cgcatgggtg atgtgttgaa tagtaaggat        660
attcaaaata tagcagtgac tattaatcaa atttaa                                  696

<210> SEQ ID NO 11
<211> LENGTH: 696
<212> TYPE: DNA
<213> ORGANISM: Staphylococcus aureus

<400> SEQUENCE: 11
gtgaaattaa aaacgttagc taaagcaaca ttggcattag cttattaaac tactggtgtg         60
attacatcag aaggccaagc agtgcaagca aaagaaaagc aagagagagt acaacattta        120
tatgatatta aagacttaca tcgatactac tcatcagaaa gttttgaatt cagtaatatt        180
agtggtaagg ttgaaaatta taacggttct aacgttgtac gctttaacca agaaaatcaa        240
aatcaccaat tattcttatc aggaaaagat aaagataaat ataagaaagg ccttgaaggc        300
cagaatgtct ttgtggtaaa agaattaatt gatccaaacg gtagactatc tactgttggt        360
ggtgtaacga agaaaaataa ccaatcttct gaaactaata cacctttatt tataaaaaaa        420
gtgtatggcg gaaatttaga tgcatcaatt gaatcatttt taattaataa agaagaagtt        480
tcactgaaag aacttgattt caaaattaga caacatttag ttaaaaatta tggtttatat        540
aaaggtacga ctaaatacgg taagatcact ttcaatttga aagatggaga aaagcaagaa        600
attgatttag gtgataaatt gcaattcgag cacatgggcg atgtgttgaa tagtaaggat        660
attcaaaata tagcagtgac tattaatcaa atttaa                                  696

<210> SEQ ID NO 12
<211> LENGTH: 606
<212> TYPE: DNA
<213> ORGANISM: Staphylococcus aureus
```

-continued

```
<400> SEQUENCE: 12
aaagaaaaac aggaacgtgt tcagcacctg tacgacatca agacctgca ccgttactac      60 tcctccgaat ccttcgaatt ctccaacatc tccggtaaag ttgaaaacta caacggttcc     120
aacgttgttc gtttcaacca ggaaaaacag aaccaccagc tgttcctgct gggtgaagac     180
aaagctaaat acaaacaggg tctgcagggt caggacgttt tcgttgttaa agaactgatc     240
gacccgaacg gtcgtctgtc caccgttggt ggtgttacca aaaaaaacaa ccagtcctcc     300
gaaaccaaca tccacctgct ggttaacaaa ctggacggtg gtaacctgga cgctaccaac     360
gactccttcc tgatcaacaa agaagaagtt tccctgaaag aactggactt caaaatccgt     420
aaacagctgg ttgaaaaata cggtctgtac cagggtacct ccaaatacgg taaaatcacc     480
atcatcctga cggtggtaa aaaacaggaa atcgacctgg gtgacaaact gcagttcgaa     540
cgtatgggtg acgttctgaa ctccaaagac atcaacaaaa tcgaagttac cctgaaacag     600
atctaa                                                              606

<210> SEQ ID NO 13
<211> LENGTH: 606
<212> TYPE: DNA
<213> ORGANISM: Staphylococcus aureus

<400> SEQUENCE: 13
aaagaaaaac aggaacgtgt tcagcacctg tacgacatca agacctgca ccgttactac      60 tcctccgaat ccttcgaatt ctccaacatc tccggtaaag ttgaaaacta caacggttcc     120
aacgttgttc gtttcaacca ggaaaaacag aaccaccagc tgttcctgct gggtgaagac     180
aaagctaaat acaaacaggg tctgcagggt caggacgttt tcgttgttaa agaactgatc     240
gacccgaacg gtcgtctgtc caccgttggt ggtgttacca aaaaaaacaa ccagtcctcc     300
gaaaccaaca tccacctgct ggttaacaaa ctggacggtg gtaacctgga cgctaccaac     360
gactccttcc tgatcaacaa agaagaagtt tccctgaaag aactggactt caaaatccgt     420
aaacagctgg ttgaaaaata cggtctgtac cagggtacct ccaaatacgg taaaatcacc     480
atcatcctga cggtggtaa aaaacaggaa atcgacctgg gtgacaaact gcagttcgaa     540
cgtatgggtg acgttctgaa ctccaaagac atcaacaaaa tcgaagttac cctgaaacag     600
atctaa                                                              606

<210> SEQ ID NO 14
<211> LENGTH: 201
<212> TYPE: PRT
<213> ORGANISM: Staphylococcus aureus

<400> SEQUENCE: 14

Lys Glu Lys Gln Glu Arg Val Gln His Leu Tyr Asp Ile Lys Asp Leu
1               5                   10                  15

His Arg Tyr Tyr Ser Ser Glu Ser Phe Glu Phe Ser Asn Ile Ser Gly
            20                  25                  30

Lys Val Glu Asn Tyr Asn Gly Ser Asn Val Val Arg Phe Asn Gln Glu
        35                  40                  45

Asn Gln Asn His Gln Leu Phe Leu Ser Gly Lys Asp Lys Asp Lys Tyr
    50                  55                  60

Lys Glu Gly Leu Glu Gly Gln Asn Val Phe Val Lys Glu Leu Ile
65                  70                  75                  80

Asp Pro Asn Gly Arg Leu Ser Thr Val Gly Val Thr Lys Lys Asn
                85                  90                  95
```

Asn Gln Ser Ser Glu Thr Asn Thr Pro Leu Phe Ile Lys Lys Val Tyr
                100                 105                 110

Gly Gly Asn Leu Asp Ala Ser Ile Glu Ser Phe Leu Ile Asn Lys Glu
            115                 120                 125

Glu Val Ser Leu Lys Glu Leu Asp Phe Lys Ile Arg Gln His Leu Val
        130                 135                 140

Lys Asn Tyr Gly Leu Tyr Lys Gly Thr Thr Lys Tyr Gly Lys Ile Thr
145                 150                 155                 160

Phe Asn Leu Lys Asp Gly Glu Lys Gln Glu Ile Asp Leu Gly Asp Lys
                165                 170                 175

Leu Gln Phe Glu His Met Gly Asp Val Leu Asn Ser Lys Asp Ile Gln
            180                 185                 190

Asn Ile Ala Val Thr Ile Asn Gln Ile
        195                 200

<210> SEQ ID NO 15
<211> LENGTH: 201
<212> TYPE: PRT
<213> ORGANISM: Staphylococcus aureus

<400> SEQUENCE: 15

Lys Glu Lys Gln Glu Arg Val Gln His Leu Tyr Asp Ile Lys Asp Leu
1               5                   10                  15

His Arg Tyr Tyr Ser Ser Glu Ser Phe Glu Phe Ser Asn Ile Ser Gly
            20                  25                  30

Lys Val Glu Asn Tyr Asn Gly Ser Asn Val Val Arg Phe Asn Gln Glu
        35                  40                  45

Asn Gln Asn His Gln Leu Phe Leu Leu Gly Lys Asp Lys Glu Lys Tyr
    50                  55                  60

Lys Glu Gly Ile Glu Gly Lys Asp Val Phe Val Lys Glu Leu Ile
65                  70                  75                  80

Asp Pro Asn Gly Arg Leu Ser Thr Val Gly Val Thr Lys Asn
                85                  90                  95

Asn Lys Ser Ser Glu Thr Asn Thr His Leu Phe Val Asn Lys Val Tyr
                100                 105                 110

Gly Gly Asn Leu Asp Ala Ser Ile Asp Ser Phe Ser Ile Asn Lys Glu
            115                 120                 125

Glu Val Ser Leu Lys Glu Leu Asp Phe Lys Ile Arg Gln His Leu Val
        130                 135                 140

Lys Asn Tyr Gly Leu Tyr Lys Gly Thr Thr Lys Tyr Gly Lys Ile Thr
145                 150                 155                 160

Ile Asn Leu Lys Asp Gly Glu Lys Gln Glu Ile Asp Leu Gly Asp Lys
                165                 170                 175

Leu Gln Phe Glu Arg Met Gly Asp Val Leu Asn Ser Lys Asp Ile Asn
            180                 185                 190

Lys Ile Glu Val Thr Leu Lys Gln Ile
        195                 200

<210> SEQ ID NO 16
<211> LENGTH: 201
<212> TYPE: PRT
<213> ORGANISM: Staphylococcus aureus

<400> SEQUENCE: 16

Lys Glu Lys Gln Glu Arg Val Gln Glu Leu Tyr Asp Ile Lys Asp Leu
1               5                   10                  15

```
Tyr Arg Tyr Tyr Ser Ser Glu Ser Phe Glu Phe Ser Asn Ile Ser Gly
            20                  25                  30

Lys Val Glu Asn Tyr Asn Gly Ser Asn Val Val Arg Phe Asn Gln Glu
        35                  40                  45

Lys Gln Asn His Gln Leu Phe Leu Leu Gly Lys Asp Lys Asp Lys Tyr
    50                  55                  60

Lys Lys Gly Leu Glu Gly Gln Asn Val Phe Val Lys Glu Leu Ile
65                  70                  75                  80

Asp Pro Asn Gly Arg Leu Ser Thr Val Gly Gly Val Thr Lys Lys Asn
                85                  90                  95

Asn Lys Ser Ser Glu Thr Asn Thr His Leu Phe Val Asn Lys Val Tyr
            100                 105                 110

Gly Gly Asn Leu Asp Ala Ser Ile Asp Ser Phe Leu Ile Asn Lys Glu
        115                 120                 125

Glu Val Ser Leu Lys Glu Leu Asp Phe Lys Ile Arg Lys Gln Leu Val
    130                 135                 140

Glu Lys Tyr Gly Leu Tyr Lys Gly Thr Thr Lys Tyr Gly Lys Ile Thr
145                 150                 155                 160

Ile Asn Leu Lys Asp Glu Lys Lys Glu Val Ile Asp Leu Gly Asp Lys
                165                 170                 175

Leu Gln Phe Glu Arg Met Gly Asp Val Leu Asn Ser Lys Asp Ile Gln
            180                 185                 190

Asn Ile Ala Val Thr Ile Asn Gln Ile
        195                 200

<210> SEQ ID NO 17
<211> LENGTH: 201
<212> TYPE: PRT
<213> ORGANISM: Staphylococcus aureus

<400> SEQUENCE: 17

Lys Glu Lys Gln Glu Arg Val Gln His Leu Tyr Asp Ile Lys Asp Leu
1               5                   10                  15

Tyr Arg Tyr Tyr Ser Ser Glu Ser Phe Glu Phe Ser Asn Ile Ser Gly
            20                  25                  30

Lys Val Glu Asn Tyr Asn Gly Ser Asn Val Val Arg Phe Asn Gln Glu
        35                  40                  45

Lys Gln Asn His Gln Leu Phe Leu Leu Gly Lys Asp Lys Asp Lys Tyr
    50                  55                  60

Lys Lys Gly Leu Glu Gly Gln Asn Val Phe Val Lys Glu Leu Ile
65                  70                  75                  80

Asp Pro Asn Gly Arg Leu Ser Thr Val Gly Gly Val Thr Lys Lys Asn
                85                  90                  95

Asn Lys Ser Ser Glu Thr Asn Thr His Leu Phe Val Asn Lys Val Tyr
            100                 105                 110

Gly Gly Asn Leu Asp Ala Ser Ile Asp Ser Phe Leu Ile Asn Lys Glu
        115                 120                 125

Glu Val Ser Leu Lys Glu Leu Asp Phe Lys Ile Arg Lys Gln Leu Val
    130                 135                 140

Glu Lys Tyr Gly Leu Tyr Lys Gly Thr Thr Lys Tyr Gly Lys Ile Thr
145                 150                 155                 160

Ile Asn Leu Lys Asp Glu Lys Lys Glu Val Ile Asp Leu Gly Asp Lys
                165                 170                 175

Leu Gln Phe Glu Arg Met Gly Asp Val Leu Asn Ser Lys Asp Ile Gln
```

```
                        180                 185                 190
Asn Ile Ala Val Thr Ile Asn Gln Ile
            195                 200

<210> SEQ ID NO 18
<211> LENGTH: 201
<212> TYPE: PRT
<213> ORGANISM: Staphylococcus aureus

<400> SEQUENCE: 18

Ala Glu Lys Gln Glu Arg Val Gln His Leu His Asp Ile Arg Asp Leu
1               5                   10                  15

His Arg Tyr Tyr Ser Ser Glu Ser Phe Glu Tyr Ser Asn Val Ser Gly
            20                  25                  30

Lys Val Glu Asn Tyr Asn Gly Ser Asn Val Val Arg Phe Asn Pro Lys
        35                  40                  45

Asp Gln Asn His Gln Leu Phe Leu Leu Gly Lys Asp Lys Glu Gln Tyr
    50                  55                  60

Lys Glu Gly Leu Gln Gly Gln Asn Val Phe Val Gln Glu Leu Ile
65                  70                  75                  80

Asp Pro Asn Gly Arg Leu Ser Thr Val Gly Gly Val Thr Lys Lys Asn
                85                  90                  95

Asn Lys Thr Ser Glu Thr Asn Thr Pro Leu Phe Val Asn Lys Val Asn
            100                 105                 110

Gly Glu Asp Leu Asp Ala Ser Ile Asp Ser Phe Leu Ile Gln Lys Glu
        115                 120                 125

Glu Ile Ser Leu Lys Glu Leu Asp Phe Lys Ile Arg Gln Gln Leu Val
    130                 135                 140

Asn Asn Tyr Gly Leu Tyr Lys Gly Thr Ser Lys Tyr Gly Lys Ile Ile
145                 150                 155                 160

Ile Asn Leu Lys Asp Glu Asn Lys Val Glu Ile Asp Leu Gly Asp Lys
                165                 170                 175

Leu Gln Phe Glu Arg Met Gly Asp Val Leu Asn Ser Lys Asp Ile Arg
            180                 185                 190

Gly Ile Ser Val Thr Ile Asn Gln Ile
        195                 200
```

SET1 PROTEINS AND USES THEREOF

CROSS-REFERENCE TO RELATED APPLICATIONS

This application is the National Stage of International Application No. PCT/NZ2004/000317, filed on Dec. 7, 2004, which claims the benefit of Australian Application Serial No. 2004901570, filed on Mar. 24, 2004. The contents of both of the foregoing applications are hereby incorporated by reference in their entirety.

FIELD

The present invention relates to methods of use of SET1 (also known as SSL7) proteins or functional equivalents thereof. More particularly the invention relates to the use of SET1 proteins or functional equivalents thereof in procedures for identification and/or isolation of IgA and the serum complement factor C5.

BACKGROUND

The gram-positive bacterium *Staphylococcus aureus* is a common human pathogen causing food poisoning, skin infections, abscesses, bacteraemia, pneumonia, endocarditis, osteomyelitis, toxic shock syndrome, staphylococcal scarlet fever and scalded skin syndrome. *S. aureus* produces a plethora of cell-surface and secreted proteins that bind host cell-surface receptors, extracellular matrix proteins, and soluble serum factors involved in both innate and adaptive immunity (1). Several studies (2) and the recent completion of several staphylococcal genomes has revealed that many of these virulence factors are clustered within 3 distinct pathogenicity islands SaPIn1, SaPIn2 and SaPIn3 (3, 4). One important class of genes within SaPIn1 and SaPIn3 are those that code for superantigens. These potent exotoxins target the antigen recognition receptors of the adaptive immune response—the Major Histocompatibility Complex class II (MHC-II) and T cell Receptor (TcR) and drive antigen independent T-cell activation and cytokine release (5) possibly in an attempt to prevent local inflammation and leukocyte recruitment to the site of infection through the production of T cell cytokines (4).

The staphylococcal exotoxin-like proteins (SETs) encoded by genes clustered within the staphylococcal pathogenicity island SaPIn2 are superantigen homologues (8). Comparative alignment of SETs and superantigen sequences indicate that they have evolved from the same ancestral gene (3) and are most similar to toxic shock syndrome toxin 1 (TSST-1) whose gene resides on SaPIn1. TSST-1 is a TcR Vβ2 binding superantigen produced by toxigenic strains of *S. aureus* associated with Toxic Shock Syndrome (9). Twenty-six members of the SET family have been identified (8) (3) (10), although several appear to be allelic variants. For example SET1 from strain NCTC6571 (8), SET11 from N315 and Mu50 (3), and SET22 from MW2 (10) are probably the same protein. The 3-D structure of SET3 has been determined and displays the same OB-fold/β-grasp two-domain structure as the superantigen (11) with conservation of the central core region at the interface of the two domains. Yet the SETs are not superantigens. They do not bind MHC class II nor activate T cells. Those regions on SET3 corresponding to the MHC class II or TcR binding sites on superantigens are substantially altered (11). The function of SETs remains unknown although the presence of their genes on SaPIn2 may indicate that they are part of the bacterial defense armamentarium (11) (8) (12). Notably an set15$^-$ mutant of *S. aureus* displayed a 30-fold reduction in bacterial persistence in a murine kidney abscess infection model.

SET proteins may also be known as staphylococcal superantigen-like proteins (or SSLs). There has been a move recently to use SSL when naming these proteins.

IgA is the predominant antibody located at mucosal surfaces and the second most predominant isotype in serum. In humans the IgA production of approximately 66 mg/kg/day exceeds that of all other Ig classes combined (13). Mucosal IgA exists mostly as a dimer complexed with a J-chain and a secretory component (SC). Polymeric IgA binds to the polyIg receptor on the basolateral surface of the mucosal epithelium to be transcytosed through the epithelial layer and released into the mucosa as a covalent complex called secretory IgA (sIgA). The cleaved ectodomain of the pIgR remains bound as the secretory component (SC). Secretory IgA is unable to bind FcαR and activate phagocytosis in the absence of an integrin co-factor Mac-1 (complement receptor 3 or CD11b) (17). (Reviewed in (15), (16)). Serum IgA on the other hand is predominantly monomeric and only binds avidly to its receptor FcαRI (CD89) on formation of immune complexes. Binding and cross-linking of FcαRI (CD89) by IgA immune complexes initiates phagocytosis by neutrophils, granulocytes and monocyte/macrophages (17). Monomeric serum IgA has been proposed to provide a second line of defense against microbes such as *S. aureus* via FcαRI mediated phagocytosis (18, 19). Mutagenesis (20-22) and the recent crystal structure of an IgA:FcαR complex reveals that the FcαR Ig-like D1 domain binds at the Cα2:Cα3 junction of the IgA H-chain (15).

Complement C5 is the central component in the terminal stage of the classical, alternative, and lectin mediated complement pathways. Complement C5 is ~189 kD and is synthesised as an intracellular single-chain precursor that is secreted as a two-chain glycoprotein consisting of a 75 kD N-terminal C5β fragment disulfide linked to a 115 kD C-terminal C5α fragment ((23, 24)). The surface bound C5 convertases generated from either the classical, alternative or lectin pathway; cleave soluble C5 to generate two active fragments C5a and C5b. The potent anaphylatoxin C5a is a 74-residue N-terminus fragment cleaved from C5α by C5 convertase. C5a binds a G-protein coupled receptor C5aR on the surface of myeloid cells to stimulate a range of pro-inflammatory and chemotactic actions such as oxidative burst, phagocytosis and leukocyte recruitment which all contribute to the defense against organisms such as *S. aureus* (25). The C5b fragment initiates assembly of the terminal complement components into the membrane attack complex (MAC) that forms a water permeable membrane channel leading to cell lysis.

Methods are known for the purification of immunoglobulins, including IgA. For example, purification may be achieved by methods including classical protein purification techniques, such as ion exchange and size exclusion chromatography, and by affinity purification using a number of bacterial derived proteins, such as Protein L. These techniques may suffer from a number of problems including being laborious, lacking specificity and can result in low yields and purity. For example, Protein L, derived from the bacterium *Peptostreptococcus magnus*, and which is used for purification of immunoglobulins, binds to a wide variety of immunoglobulins. This means that it may not be suitable for the purification of a single species of immunoglobulin from a heterogenous mix of immunoglobulins.

An example of a product which may allow for single step purification of IgA and IgE is the affinity purification product known as Kaptiv-ae™ (Genomics One International Inc, USA). This is a synthetic peptidomimetic compound that selectively binds IgA and IgE from several species.

Single step purification methods for complement C5 are not known. Current methods to purify complement C5 from human serum, for example, rely on multiple chromatographic steps such as ion exchange and size exclusion chromatography. These may often result in low yields of final product.

Accordingly, there may be considered a need to provide an alternative or improved method of isolating and identifying IgA and C5.

Bibliographic details of the publications referred to herein are collected at the end of the description.

OBJECT

It is an object of the present invention to provide an improved method of removing, isolating and/or detecting IgA and/or C5 or at least to provide the public with a useful choice.

STATEMENT OF INVENTION

In accordance with the present invention it has been discovered that recombinant SET1, either in precursor or mature form, binds independently IgA and the serum complement factor C5. This may have significant application in methods of isolating or removing IgA and C5 from samples and also in identification and quantitation of IgA and C5 in samples for diagnostic purposes, for example.

In a first aspect of the invention there is provided a method of isolating IgA present in a sample, the method comprising at least the steps of:

Bringing SET1 or a functional equivalent thereof in contact with the sample for a period sufficient to allow SET1 or functional equivalent thereof to bind to IgA to form a complex;

Separating the complex; and

Releasing IgA from the complex.

In another aspect of the invention there is provided a method of isolating C5 present in a sample, the method comprising at least the steps of:

Bringing SET1 or a functional equivalent thereof in contact with the sample for a period sufficient to allow SET1 or functional equivalent thereof to bind to C5 to form a complex;

Separating the complex; and

Releasing C5 from the complex.

In a preferred aspect of the present invention there is provided a method for isolating IgA from a sample, the method comprising at least the steps of:

Providing a matrix to which a SET1 protein or functional equivalent thereof is bound;

Providing a sample;

Bringing said matrix and said sample into contact for a period sufficient to allow SET1 or functional equivalent thereof to bind to IgA present in the sample; and, Releasing IgA from the matrix.

Preferably, the method further comprises the step of collecting the IgA released.

Preferably, the matrix is in the form of a column over which the sample is passed.

Preferably the method further comprises the step of washing contaminants present in the sample from the matrix prior to release of IgA.

Preferably the matrix is Sepharose.

Preferably the sample is milk or colostrum. More preferably the sample is serum.

Preferably the method further comprises the step of determining the quantity of IgA present in the sample.

Preferably, IgA is released from the matrix using a 100 mM glycine buffer at pH 3.0.

In a preferred aspect of the present invention there is provided a method for isolating C5 from a sample, the method comprising at least the steps of:

Providing a matrix to which a SET1 protein or functional equivalent thereof is bound;

Providing a sample;

Bringing said matrix and said sample into contact for a period sufficient to allow SET1 or functional equivalent thereof to bind to C5 present in the sample; and, Releasing C5 from the matrix.

Preferably, the method further comprises the step of collecting the C5 released.

Preferably, the matrix is in the form of a column over which the sample is passed.

Preferably the method further comprises the step of washing contaminants present in the sample from the matrix prior to release of C5.

Preferably the matrix is Sepharose.

Preferably the sample is milk or colostrum. More preferably the sample is serum.

Preferably the method further comprises the step of determining the quantity of C5 present in the sample.

Preferably, C5 is released low pH buffer such as 5 mM acetate pH 3.5.

In another aspect the invention provides a method of detecting IgA and/or C5 in a sample, the method comprising at least the steps of:

Contacting a sample with SET1 or functional equivalent thereof for a period sufficient to allow SET1 or functional equivalent thereof to bind to IgA and/or C5; and, Detecting bound SET1 or functional equivalent thereof.

Preferably, the method further includes the step of determining or quantifying the level of bound SET1.

Preferably, the method is conducted for the purpose of diagnosing IgA and/or C5 abnormalities in a subject.

Preferably the subject is a mammal, more preferably a human.

In another aspect of the invention there is provided a method of removing IgA from a sample, the method comprising at least the steps of:

Bringing SET1 or a functional equivalent thereof in contact with the sample for a period sufficient to allow SET1 or functional equivalent thereof to bind to IgA to form a complex;

Separating the complex from the sample.

In another aspect of the invention there is provided a method of removing C5 from a sample, the method comprising at least the steps of:

Bringing SET1 or a functional equivalent thereof in contact with the sample for a period sufficient to allow SET1 or functional equivalent thereof to bind to C5 to form a complex;

Separating the complex from the sample.

In another aspect, the invention provides a kit for the detection of IgA and/or C5 in a sample, the kit comprising at least SET1 or a functional equivalent thereof.

In a further aspect, the invention provides a kit for the isolation of IgA and/or C5 from a sample, the kit comprising at least SET1 or a functional equivalent thereof.

In another aspect, the invention provides a kit for the removal of IgA and/or C5 from a sample, the kit comprising at least SET1 or a functional equivalent thereof.

In a further aspect, the present invention provides a novel SET1 protein having the amino acid sequence SEQ ID NO: 6 or SEQ ID NO: 7.

In a related broad aspect, the invention provides a nucleic acid encoding a SET1 protein of SEQ ID NO:6 or SEQ ID NO:7.

Preferably, the nucleic acid sequence is that represented by SEQ ID NO:12 or SEQ ID NO:13.

The invention may also be said broadly to consist in the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

FIGURES

These and other aspects of the present invention, which should be considered in all its novel aspects, will become apparent from the following description, which is given by way of example only, with reference to the accompanying figures, in which:

FIG. 1. Illustrates Purified recombinant proteins. 10 µg of recombinant FcαRI ectodomain produced in baculovirus (22) (lane 2) and 10 µg of SET1 produced in E. coli (lane 3) were analyzed by SDS PAGE under reducing conditions. Samples of purified human polyclonal IgA were also run for size comparison.

Figure 2:
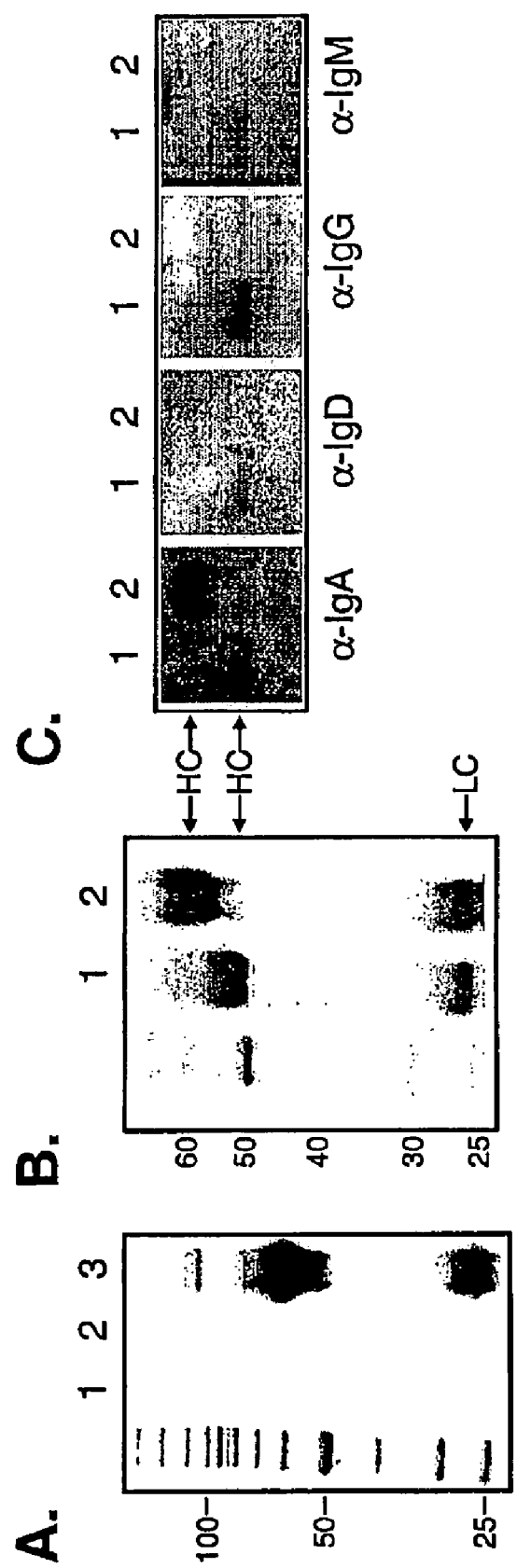

FIG. 2. Illustrates Serum proteins bound by SET1. A. Recombinant SET1 coupled to sepharose purified proteins from human serum (lane 3) but not from fetal calf serum (lane 2) of PBS (lane 1) controls. B. Comparison of protein A (lane 1) and SET1 purified Ig (lane 2) showing that the heavy chain for protein A purified IgG is 50 k while that for SSL7 was 60 kD. C. Proteins purified from human serum by either protein A (lane 1) or SET1 (lane 2) were analyzed by Western blotting using human isotype specific anti-sera Only the anti-IgA anti-serum (panel 1) detected the SSL7 bound IgA heavy chain at 60 kD. Anti-IgD, IgG and IgM did not react to SET1 purified serum proteins. All SDS PAGE gels were run under reducing conditions.

Figure 3:
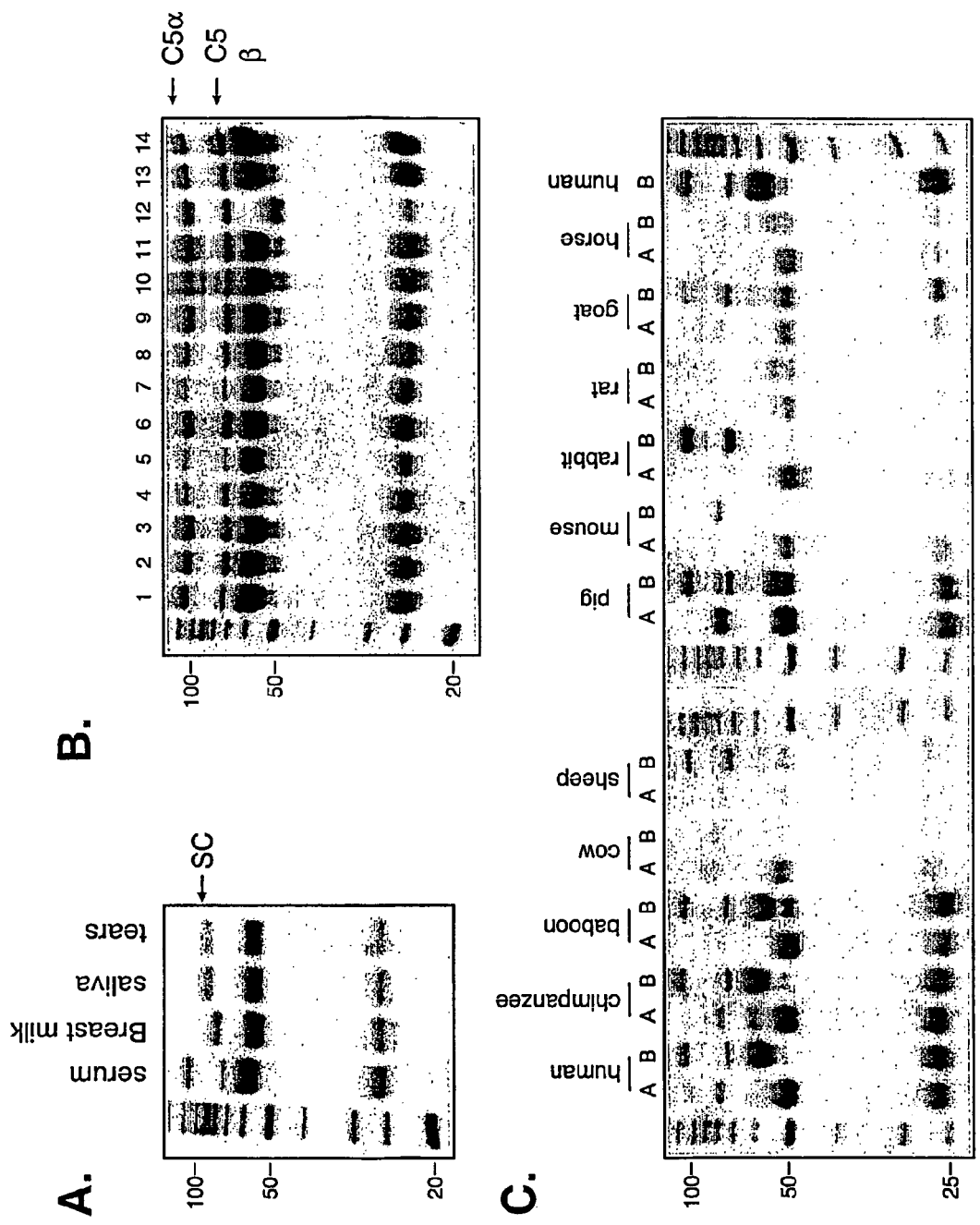

FIG. 3. Illustrates SET1 binds IgA and C5 from multiple sites, individuals and species. A. SET1 sepharose purified proteins from serum (10 µl), breast milk (10 µl), saliva (100 µl), and tears (100 µl), and analyzed by SDS PAGE under reducing conditions. The arrow indicates the position of the secretory component (SC) associated with secretory IgA observed in breast milk, saliva and tear but absent from serum. The serum sample contains the additional C5 alpha and C5 beta chains that are absent in the breast milk, saliva and tears. B. SET1 purified proteins from the serum of 14 human volunteers. 10 µl of serum was incubated with 10 µl (50% v/v=50 µg) of SET1 sepharose. The positions of C5 alpha (110 kD) and C5 beta (70 kD) chains, visible in all 14 samples, are shown by the arrows, Note absence of IgA heavy chain in lane 12. The 50 kD protein that varied in concentration between individuals is IgG Heavy chain and presumably results from natural sero-conversion against SET1. C. SET1 binds IgA from human, chimpanzee, baboon, pig, (and possibly rat and horse) and C5 from human, chimpanzee, baboon, sheep, pig, rabbit and goat. SpA-sepharose (lanes A) or SET1-sepharose (=50 µg) (lanes B) was incubated with 10 µl of serum from different species and eluted proteins examined by SDS PAGE under reducing conditions.

Figure 4:
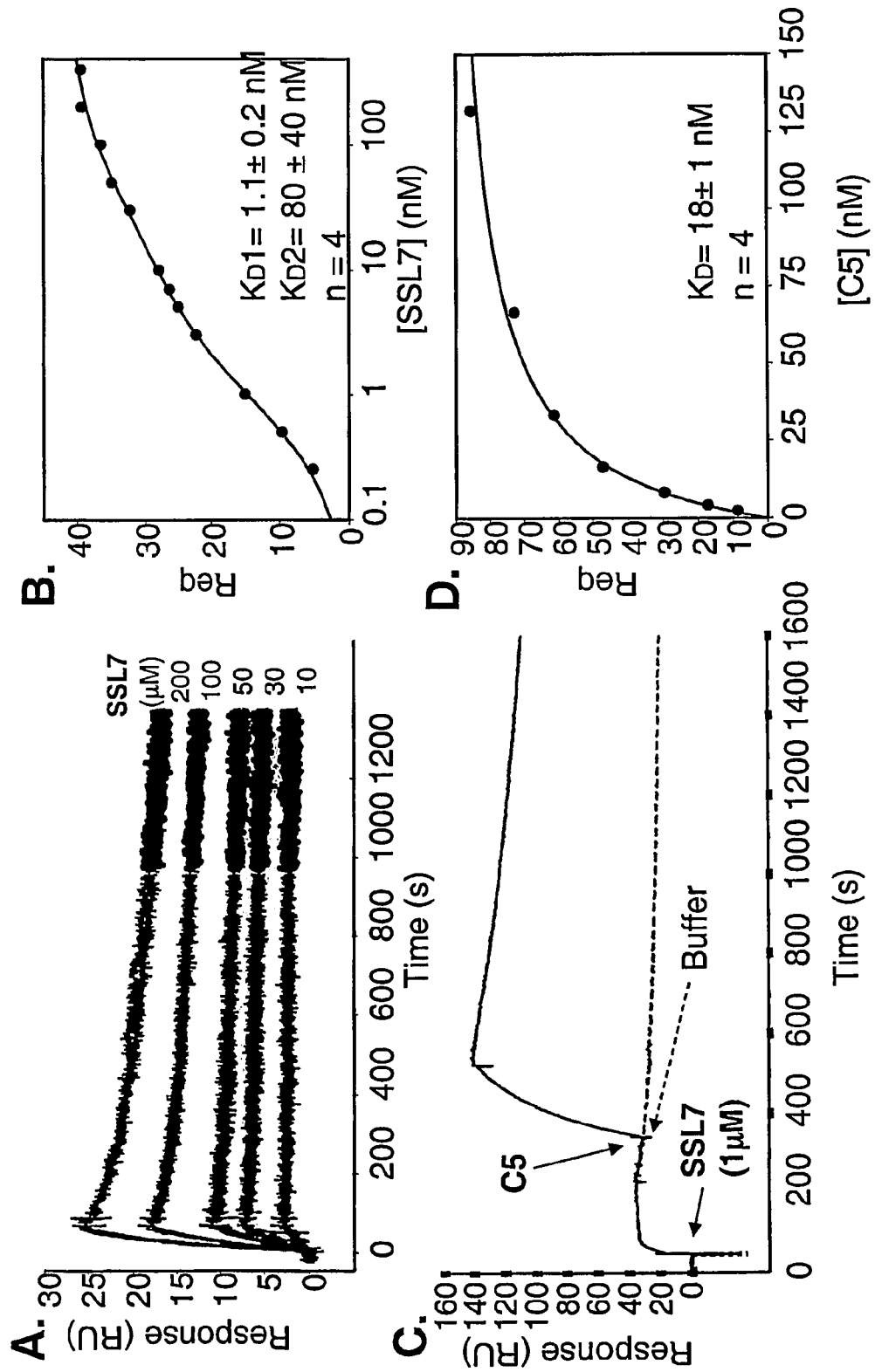

FIG. 4. Illustrates that biosensor analysis demonstrates nanomolar binding of SET1 to IgA and C5 through independent sites. Serum IgA was immobilized to a CM5 BIAcore biosensor chip using carbodiimide chemistry. A) Kinetic IgA binding analysis: SET1 was reacted with the immobilized layer at the indicated concentrations at a flow rate of 30 µl/min. The data from 20 sensosograms (light grey curves) from 4 independent experiments are shown globally fitted (black solid line), using the BIAevaluation version 2.1 software, to a model describing parallel binding to a heterogeneous ligand model. Two types of sites are indicated the first $K_D1=1.0$ nM, the second $K_D2=330$ nM, chi2=0.184, n=4. B) Equilibrium IgA binding analysis: SET1 was reacted with the immobilized layer at the indicated 12 concentrations at a flow rate of 1 µl/min. For each concentration of SET1 the equilibrium binding response to IgA was obtained after 120 min. The data shown is one representative experiment. Analysis of 4 independent experiments indicated 2 types of sites; the first $K_D1=1.1\pm0.2$ nM, the second $K_D2=80\pm40$ nM. C) SET1 captured on IgA can simultaneously bind human C5: SET1 (1 µM) was reacted with the immobilized IgA layer (30 µl, flow rate of 10 µl/min) and a subsequent injection was made of either buffer (dashed line) or human C5 (0.3 µM, 30 µl). D) Equilibrium C5 binding analysis: SET1 (1 µM) was reacted with the immobilized IgA layer (30 µl, flow rate of 10 µl/min) and a subsequent injection (122 µl, flow rate of 1 µl/min) was made of the indicated concentrations of human C5 (122 µl). For each concentration of C5 the equilibrium binding response to the SET1:IgA was obtained after 120 min. The data shown is one representative experiment fitted to a single binding site. Analysis of 4 independent experiments indicated $K_D=18\pm1$ nM.

FIG. 5. Illustrates different alleles of SSL7. A. Amino sequence alignment of known alleles of mature SET1, including SSL7_GL10 (SEO ID NO:6), SSL7_GL1 (SEQ ID NO:7), SSL7_MW2 (SEQ ID NO:14), SSL7_NCTC8325 (SEQ ID NO:15), SSL7_Mu50 (SEQ ID NO:16), SSL7_N315 (SEQ ID NO:17), SSL7-NCTC6571 (SEQ ID NO:18). Two local clinical isolates (GL1 and GL10) are included in the alignment. Identity (*), strong similarity (:), and weak similarity (.), at each amino acid position is indicated. B. Proteins eluted from immobilized alleles (GL1 and GL10) that differ in 30/201 amino acids (underlined in A) run on SDS PAGE under reducing conditions. Both alleles bound IgA and C5 from two human sera. A.

Figure 6:
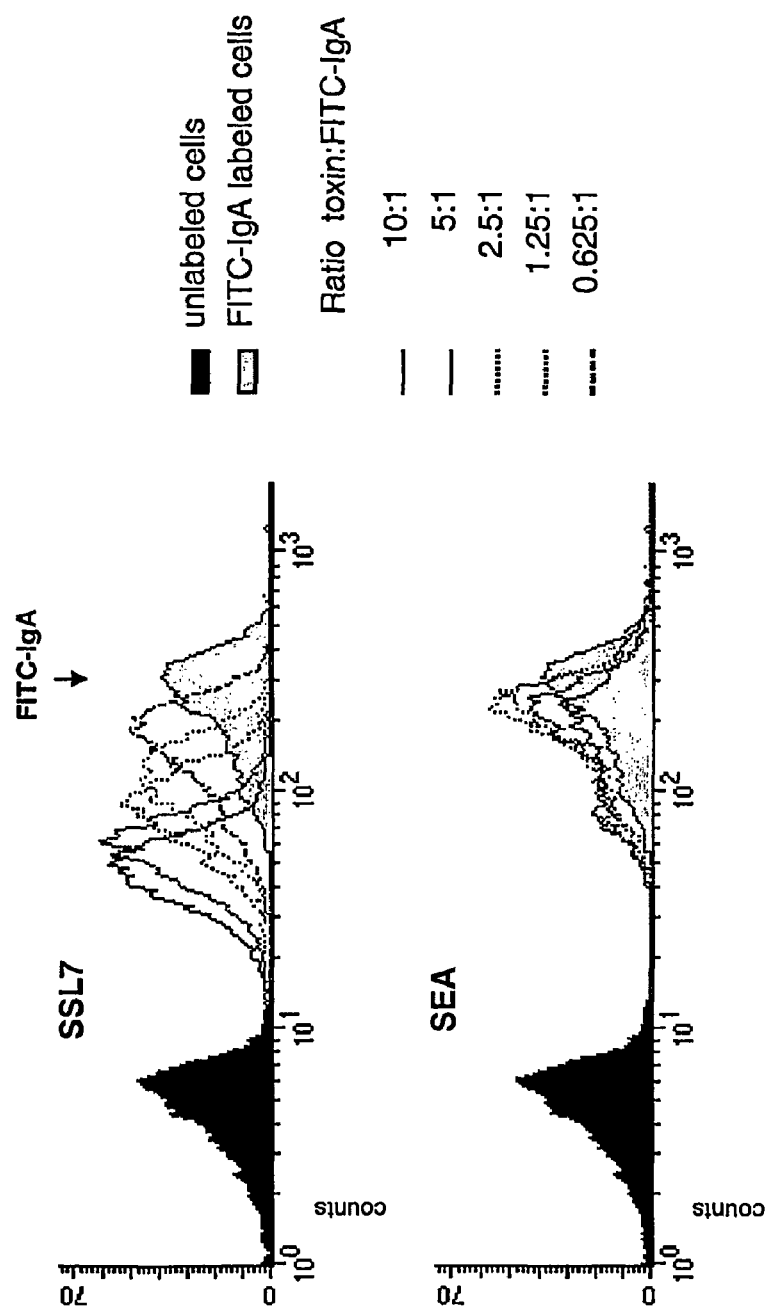

FIG. 6. Illustrates flow cytometric analysis of IgA binding to granulocytes. IgA-FITC was added at 10 µg to freshly prepared human granulocytes (gray histogram). SET1 (0.1-100 µg) (open histograms) was incubated with IgA-FITC prior to cell staining (upper panel). SEA was used as a negative control and does not inhibit cell staining by IgA-FITC (lower panel).

Figure 7:
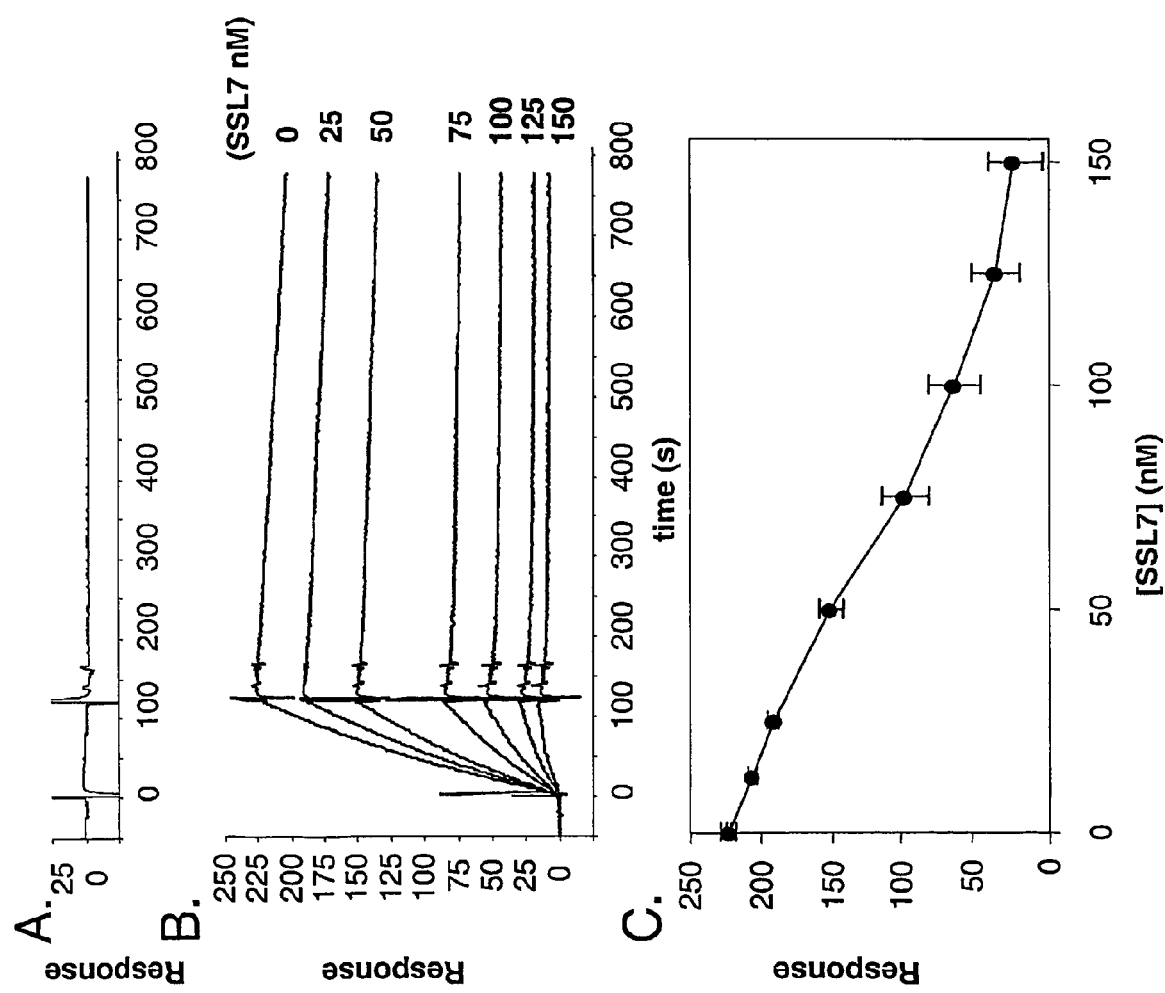

FIG. 7. Illustrates SET1 inhibits the binding of IgA to rsFcαRI. Biosensor analysis of recombinant SSL7 binding to recombinant CD89 (FcαRI) A. No binding of 200 nM SET1 to immobilized FcαRI was detected. B. Addition of increasing amounts of SET1 (0-150 nM) progressively prevented the binding of soluble IgA (100 nM to immobilized rsFcαRI. SET1 was incubated with IgA prior to binding the rsFcαRI immobilized chip surface. C. The 1 min post-injection responses of IgA binding indicate the dose-dependent inhibition by SET1. At stoichiometric addition of SET1 (100 nM) to the IgA binding (62 RU) to rsFcαRI was inhibited by 70%.

Figure 8:
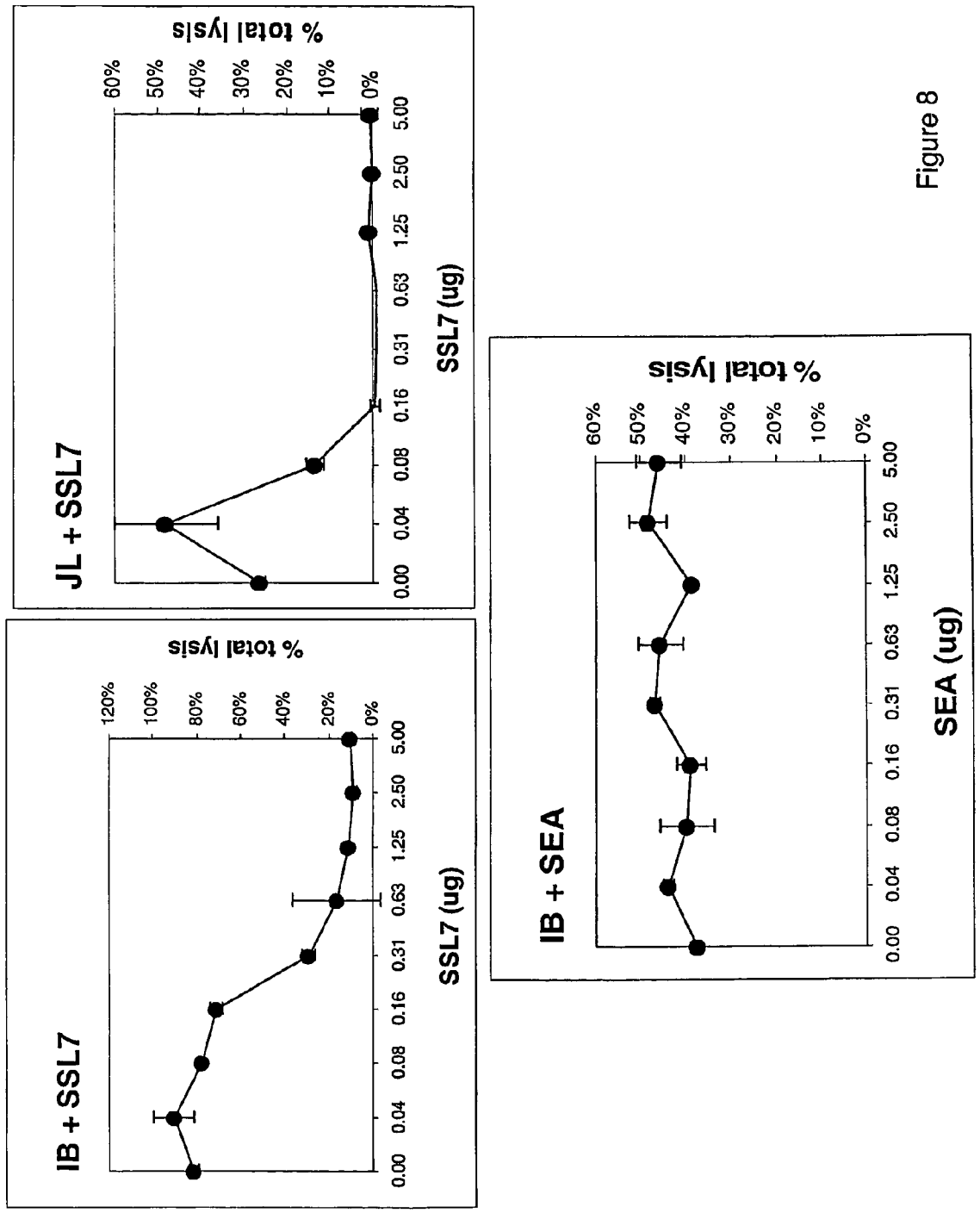

FIG. 8. Illustrates SET1 blocks complement mediated hemolysis of human erythrocytes. A. Hemolysis by IB serum of human RBC was inhibited in a dose dependent fashion by recombinant SET1. Maximum inhibition by SET1 was achieved at 0.63 µg for 25 µl serum (equivalent to 1.0 nM SET1). B. Inhibition of JL serum. Maximum inhibition was achieved at 0.16 µg SET1 equivalent to 0.26 nM). C. Addition of recombinant SET3 did not affect hemolysis. Each tube used 25 µl of human serum. Curves represent the average of duplicate.

Figure 9:
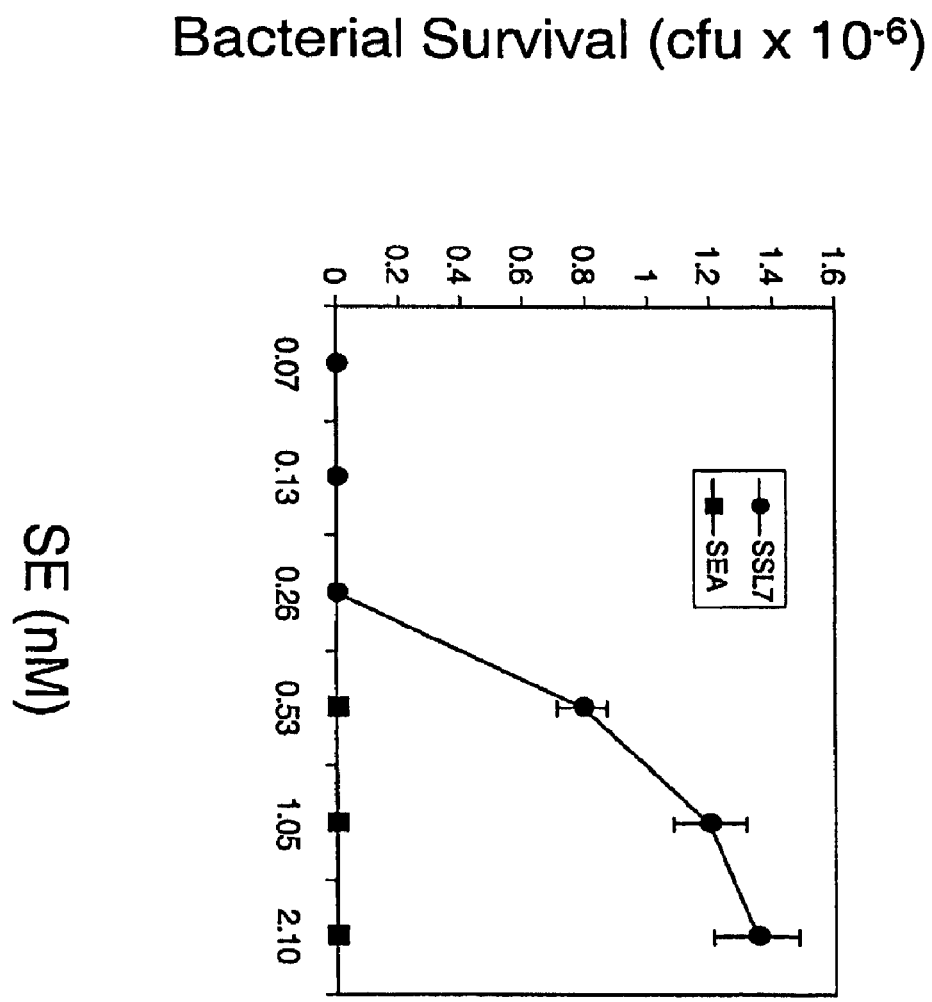

FIG. 9. Illustrates Recombinant SET1 increases bacterial survival in serum. Freshly isolated human serum (500 µl diluted 1:2) was pre-incubated in duplicate with increasing concentrations of either recombinant SET1 or staphylococcal enterotoxin A (SEA) (control) for 30 minutes at 37° C. prior to the addition of ~$10^7$ E. coli K12 bacteria Surviving bacteria were counted by plating of appropriate dilutions on agar.

Figure 10:
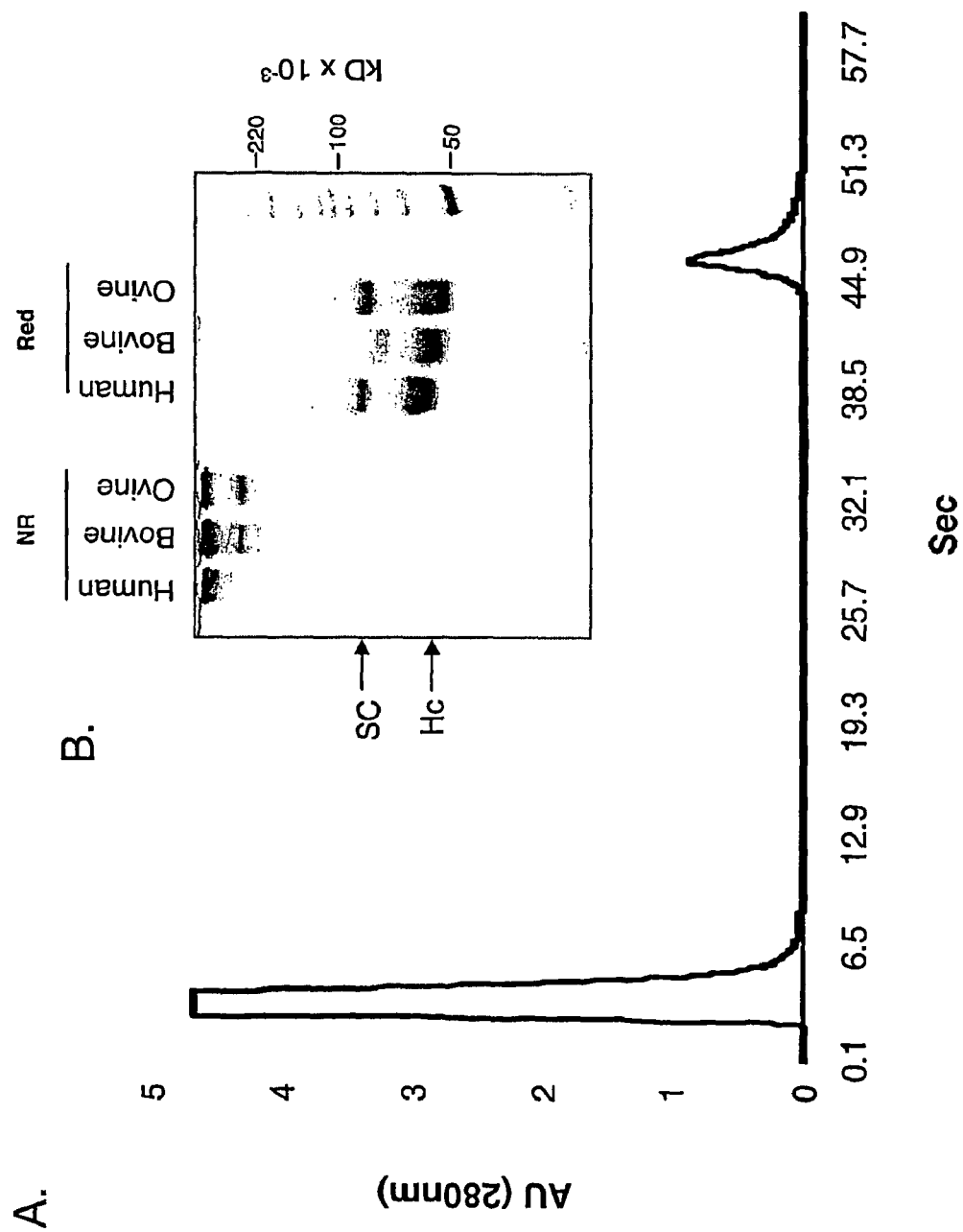

FIG. 10. Illustrates the results of single step affinity purification of IgA from human breast milk and bovine colostrums. A representative trace of SSL7 purified IgA from human breast milk, bovine or ovine colostrums is shown as absorbance units (AU) at 280 nm. 1 ml of diluted (40 mg/ml) milk or colostrums was passed through the 0.7 ml column at a flow rate of 10 ml/min and bound protein eluted with 50 mM glycine pH11. B. SDS PAGE of eluted proteins indicates equivalent amounts of bovine secretory component (75 kD) and bovine IgA heavy chain (55 kD) that migrated as a single species ~400 kD under non-reducing conditions that resolved into SC and IgA heavy chain under reducing conditions.

PREFERRED EMBODIMENT(S)

The following is a description of the present invention, including preferred embodiments thereof, given in general terms. The invention is further elucidated from the disclosure given under the section "Examples" which provides experimental data supporting the invention and specific examples thereof.

As mentioned herein before, there has been a recent move to standardise nomenclature used in relation to the SET proteins. Accordingly, they may now be known as SSL (staphylococcal superantigen-like) proteins. In line with this, the proteins SET1 (from strain NCTC6571), SET11 (from strains N315 and Mu50) and SET22 (from strain MW2), each of which may be referred to herein, may now be referred to as alleles of SET1 (SSL7). As described in Lina et al, the SSLs are now named in sequential order as they occur on the genome.

The inventors have surprisingly discovered that SET1 proteins bind independently the antibody IgA and the complement factor C5. This has significant application in the purification or isolation of both IgA and C5 from samples. An additional application is in the identification or detection, including quantitation, of IgA and C5 in a sample.

The staphylococcal exotoxin-like proteins (SETs), encoded by genes clustered within the staphylococcal pathogenicity island SaPIn2 are superantigen homologues. The function or role of SETs in unknown but they do not possess any superantigen activity despite ancestral relatedness. The inventors show here that recombinant SET1 expressed in E. coli selectively binds to human, chimpanzee, baboon, pig, horse, rat and sheep and cow IgA. They have also shown that SET1 selectively binds serum complement factor C5 from a number of different species tested (including human, goat, sheep, rabbit, chimpanzee, baboon and pig). SET1 blocked binding of IgA to cell surface bound FcαRI (CD89) and stoichiometric addition of SET1 to IgA was sufficient to inhibit binding to purified recombinant FcαR protein. SET1 was also a potent inhibitor of complement-mediated hemolysis. SET1 bound to both monomer and secretory forms of Immunoglobulin A, demonstrating that SET1 and the secretory chain (SC) binding sites on IgA do not overlap. These results indicate that SET1 is a soluble microbial defense factor with multiple activities that targets two important host innate protective mechanisms—Fc receptor mediated phagocytosis and complement mediated inflammatory responses to S. aureus.

It should be appreciated that reference to isolation, removal, detection or quantifying the level of IgA and/or C5, may include isolation, removal, detection or quantifying the level of a subunit or monomer of IgA and/or C5, or fragments of such molecules where appropriate.

Further, it should be appreciated that reference to IgA includes reference to isotypes or subclasses of IgA, for example IgA1 and IgA2, which are capable of binding to SET1 or functional equivalents thereof. Similarly, reference to C5 should be taken to include reference to any alternative forms of this molecule which are capable of binding to SET1 or functional equivalents thereof.

A first embodiment of the invention relates to a method for isolating IgA and/or C5 from a sample using a SET1 protein or functional equivalent thereof. Generally, the method comprises at least the steps of: bringing SET1 or a functional equivalent thereof in contact with the sample for a period sufficient to allow SET1 or functional equivalent thereof to bind to IgA and/or C5 to form a complex; separating the complex; and, releasing IgA and/or C5 from the complex.

In a preferred form of this embodiment the method comprises at least the steps of: providing a matrix to which a SET1 protein or functional equivalent is bound; providing a sample; bringing said matrix and said sample into contact for a period sufficient to allow SET1 or functional equivalent thereof to bind to IgA and/or C5 present in the sample; and, releasing IgA and/or C5 from the matrix.

It should be understood that the terms "isolate", or "isolating" and the like indicates that IgA and/or C5 have been separated from at least one contaminating compound. It should be appreciated that 'isolated' does not reflect the extent to which IgA and/or C5 have been purified.

A SET1 protein of the invention may be exemplified by the following amino acid sequence which is provided on Gen-Bank:

```
SET1 gi|6176432|gb|AAF05587.1|AF188835_1
[Staphylococcus aureus subsp. NCTC6571] exotoxin 1
(set1) gene, set1-A allele, complete cds
                                              [SEQ ID NO: 1]
MKLKTLAKATLALGLLTTGVITSEGQAVQAAEKQERVQHLHDIRDLHRYY

SSESFEYSNVSGKVENYNGSNVVRFNPKDQNHQLFLLGKDKEQYKEGLQG

QNVFVVQELIDPNGRLSTVGGVTKKNNKTSETNTPLFVNKVNGEDLDASI

DSFLIQKEEISLKELDFKIRQQLVNNYGLYKGTSKYGKIIINLKDENKVE

IDLGDKLQFERMGDVLNSKDIRGISVTINQI.
```

However, there is noted allelic variation in SET1 proteins. The inventors have shown that allelic variation does not alter the binding properties of SET1 to IgA or C5. Accordingly, the invention is applicable to allelic variants of SET1 proteins specifically exemplified herein (for example SET11 and SET22 isolated from different strains of S. aureus). Such allelic variants generally have at least approximately 80% similarity at the amino acid level. The invention is also applicable to those proteins not considered allelic variants per se but which incorporate conservative (as is understood in the art) amino acid substitutions at one or more sites. Additionally, the invention is applicable to proteins or peptides which represent addition/deletion mutants of the SET1 proteins specifically exemplified herein, or those in which non-naturally occurring or modified amino acids have been substituted for naturally occurring amino acids at one or more position. The aforementioned variants may be referred to herein as "functional equivalents". In accordance with the invention, "functional equivalents" retain the ability to bind to IgA and C5 from human serum. The term, "bind to" IgA and C5 should not be taken to imply a specific level of binding or affinity between the molecules or that they will have equal affinity for IgA and C5. The binding or affinity is preferably strong enough to allow for one or more of isolation, removal and/or detection of these molecules.

The inventors contemplate the use of SET1 or functional equivalents thereof in the form of fusion proteins, provided the heterologous amino acid sequence does not substantially interfere with binding to IgA and/or C5. Such fusion proteins are also considered to be "functional equivalents" of SET1.

Reference to SET1 proteins and functional equivalents thereof, and the exemplary sequences provided on public databases and otherwise herein, should be taken to include reference to mature SET1 polypeptides excluding any signal or leader peptide sequences or other sequences not present in the mature protein but which may be represented on such databases or in the sequence information contained herein. Persons of general skill in the art to which the invention relates will readily appreciate such mature proteins.

Reference to nucleic acids encoding SET1 and its functional equivalents should be taken to include those nucleic acids encompassing the amino acid coding region, and also those which additionally contain regulatory sequences such as promoters, operators or enhancers.

Typically, a SET1 protein, or function equivalent thereof, will have an amino acid sequence having at least approximately 80% similarity to that of GenBank AAF05587.1 (SEQ ID NO: 1 above). Preferably, there will be at least approximately 85% amino acid similarity, more preferably at least approximately 90% similarity.

It should be noted that SET1 proteins and their functional equivalents may be of human or any other animal origin.

Specific examples of further SET1 proteins of use in the invention include:

[SEQ ID NO: 2]-provided on GenBank database
>SET1 gi|6176432|gb|AAF05587.1|AF188835_1
Staphylococcus aureus exotoxin 1 (set1)
gene, set1-A allele, complete cds
MKLKTLAKATLALGLLTTGVITSEGQAVQAAEKQERVQHLHDIRDLHRYY

SSESFEYSNVSGKVENYNGSNVVRFNPKDQNHQLFLLGKDKEQYKEGLQG

QNVFVVQELIDPNGRLSTVGGVTKKNNKTSETNTPLFVNKVNGEDLDASI

DSFLIQKEEISLKELDFKIRQQLVNNYGLYKGTSKYGKIIINLKDENKVE

IDLGDKLQFERMGDVLNSKDIRGISVTINQI

[SEQ ID NO: 3]-provided on DDBJ database
>SET11_N315 gi|13700317|db|BAB41615.1| exotoxin 11
[Staphylococcus aureus subsp. aureus N315]
MKLKTLAKATLALGLLTTGVITSEGQAVHAKEKQERVQHLYDIKDLYRYY

SSESFEFSNISGKVENYNGSNVVRFNQEKQNHQLFLLGKDKDKYKKGLEG

QNVFVVKELIDPNGRLSTVGGVTKKNNKSSETNTHLFVNKVYGGNLDASI

DSFLINKEEVSLKELDFKIRKQLVEKYGLYKGTTKYGKITINLKDEKKEV

IDLGDKLQFERMGDVLNSKDIQNIAVTINQI

[SEQ ID NO: 4]-provided on GenBank database
>SET11_Mu50 gi|15923416|ref|NP_370950.1| exotoxin
11 [Staphylococcus aureus subsp. aureus Mu50]
MKLKTLAKATLALGLLTTGVITSEGQAVHAKEKQERVQELYDIKDLYRYY

SSESFEFSNISGKVENYNGSNVVRFNQEKQNHQLFLLGKDKDKYKKGLEG

QNVFVVKELIDPNGRLSTVGGVTKKNNKSSETNTHLFVNKVYGGNLDASI

DSFLINKEEVSLKELDFKIRKQLVEKYGLYKGTTKYGKITINLKDEKKEV

IDLGDKLQFERMGDVLNSKDIQNIAVTINQI

[SEQ ID NO: 5]-provided on GenBank database
>SET22_MW2 gi|21282117|ref|NP_645205.1|
ORFID:MW0388~exotoxin homolog
[Genomic island nu Sa alpha2] [Staphylococcus
aureus subsp. aureus MW2]
MKLKTLAKATLALGLLTTGVITSEGQAVQAKEKQERVQHLYDIKDLHRYY

SSESFEFSNISGKVENYNGSNVVRFNQENQNHQLFLSGKDKDKYKEGLEG

QNVFVVKELIDPNGRLSTVGGVTKKNNQSSETNTPLFIIKKVYGGNLDAS

IESFLINKEEVSLKELDFKIRQHLVKNYGLYKGTTKYGKITFNLKDGEKQ

EIDLGDKLQFEHMGDVLNSKDIQNIAVTINQI

[SEQ ID NO: 6]-novel SET1 allelic variant isolated
by inventors
>SET1 GL10 S.aureus Greenlane
KEKQERVQHLYDIKDLHRYYSSESFDFSNISGKVENYNGSNVVRFNQDGQ

NHQLFLLGEDKAKYKQGLEGQNVFVVKELIDPNGRLSTVGGVTKKNNQSS

ETNTPLFVKKVYGGNLDASIESFSINKEEVSLKELDFKIRQHLVKNYGLY

KGTTKYGKITFNLKDGEKKEIDLGDKLQFEHMGDVLNSKDIQNIAVTLKQ

I

[SEQ ID NO: 7]-novel SET1 allelic variant isolated
by inventors
>SET1 GL1 S.aureus Greenlane
KEKQERVQHLYDIKDLHRYYSSESFEFSNISGKVENYNGSNVVRFNQEKQ

NHQLFLLGEDKAKYKQGLQGQDVFVVKELIDPNGRLSTVGGVTKKNNQSS

ETNIHLLVNKLDGGNLDATNDSFLINKEEVSLKELDFKIRKQLVEKYGLY

QGTSKYGKITIILNGGKKQEIDLGDKLQFERMGDVLNSKDINKIEVTLKQ

I

Nucleic acids encoding SET1 proteins and functional equivalents of the invention will be appreciated having regard to the information herein and the known degeneracy in the genetic code. However, exemplary nucleic acids include:

[SEQ ID NO: 8]-provided on GenBank database
>set1|AF188835|[Staphylococcus aureus subsp. aureus NCTC6571]
  1 atgaaattaa aaacgttagc taaagcaaca ttagcattag gtttattaac tactggtgtc 61 attacatcag aaggtcaagc agttcaagcg gcagaaaaac aagagagagt acaacattta 121 catgatatta gagatttaca tcgatactac tcatcagaaa gtttcgaata tagtaatgtt 181 agtggtaagg ttgaaaacta caatggttct aacgttgtac gctttaaccc aaaagatcaa 241 aatcaccaat tattcttatt aggaaaagat aaagaacaat ataagaagg tctacaaggc 301 caaaatgtct tgtagtaca agaattaatt gatccaaacg gcagactatc tactgttggt 361 ggtgtaacga agaaaaacaa caaaacttct gaaactaata cacctttatt tgttaataaa 421 gttaatggtg aagatttaga tgcatcaatt gactcatttt taatccaaaa agaagaaatc 481 tcattaaaag agcttgattt caaaattaga caacaattag ttaataatta cggattatat 541 aaaggtacat ctaaatacgg taaaatcatt atcaatttga aagacgaaaa taaagtagaa 601 attgattag gtgataaatt acaattcgag cgcatgggcg atgtgttgaa tagtaaagac 661 attagaggta tatcagtcac tattaaccaa atttaa

[SEQ ID NO: 9]-provided on GenBank database
>exotoxin 11|BAB41615.1|[Staphylococcus aureus subsp. aureus N315].
  1 atgaaattaa aaacgttagc taaagcaaca ttggcattag gcttattaac tactggtgtg 61 attacatcag aaggccaagc agtccacgca aagaaaagc aagagagagt acaacattta 121 tatgatatta agacttata tcgatactac tcatcagaaa gttttgaatt cagtaatatt 181 agtggtaagg ttgaaaacta taacggttct aacgttgtac gctttaacca agaaaaacaa 241 aatcaccaat tattcttatt aggaaaagat aaagataaat ataaaaaagg ccttgaaggc 301 cagaatgtct tgtggtaaa agaattaatt gatccaaacg gtagactatc tactgttggt 361 ggtgtgacta agaaaaataa caaatcttct gaaactaata cacatttatt tgttaataaa 421 gtgtatggcg gaaatttaga tgcatcaatt gactcatttt taattaataa agaagaagtt 481 tcactgaaag aacttgattt caaaattaga aagcaattag ttgaaaaata tggtttatat 541 aaaggtacga ctaaatacgg taagatcact atcaatttga aagacgagaa aaaggaagta 601 attgatttag gtgataaact gcaattcgag cgcatgggtg atgtgttgaa tagtaaggat 661 attcaaaata tagcagtgac tattaatcaa atttaa

[SEQ ID NO: 10]-provided on GenBank database
>exotoxin 11|NP_370950.1|[Staphylococcus aureus subsp. aureus Mu50].
  1 atgaaattaa aaacgttagc taaagcaaca ttggcattag gcttattaac tactggtgtg 61 attacatcag aaggccaagc agtccacgca aagaaaaagc aagagagagt acaacattta 121 tatgatatta agacttata tcgatactac tcatcagaaa gttttgaatt cagtaatatt 181 agtggtaagg ttgaaaacta taacggttct aacgttgtac gctttaacca agaaaaacaa 241 aatcaccaat tattcttatt aggaaaagat aaagataaat ataaaaaagg ccttgaaggc 301 cagaatgtct tgtggtaaa agaattaatt gatccaaacg gtagactatc tactgttggt 361 ggtgtgacta agaaaaataa caaatcttct gaaactaata cacatttatt tgttaataaa 421 gtgtatggcg gaaatttaga tgcatcaatt gactcatttt taattaataa agaagaagtt 481 tcactgaaag aacttgattt caaaattaga aagcaattag ttgaaaaata tggtttatat 541 aaaggtacga ctaaatacgg taagatcact atcaatttga aagacgagaa aaaggaagta 601 attgatttag gtgataaact gcaattcgag cgcatgggtg atgtgttgaa tagtaaggat 661 attcaaaata tagcagtgac tattaatcaa atttaa -continued

[SEQ ID NO: 11]-provided on GenBank database
>exotoxin 22|NC_003923.1|[*Staphylococcus aureus* subsp. *aureus* MW2]
```
  1 gtgaaattaa aaacgttagc taaagcaaca ttggcattag gcttattaac tactggtgtg 61 attacatcag aaggccaagc agtgcaagca aaagaaaagc aagagagagt acaacattta 121 tatgatatta aagacttaca tcgatactac tcatcagaaa gttttgaatt cagtaatatt 181 agtggtaagg ttgaaaatta taacggttct aacgttgtac gctttaacca agaaaatcaa 241 aatcaccaat tattcttatc aggaaaagat aaagataaat ataaagaagg ccttgaaggc 301 cagaatgtct ttgtggtaaa agaattaatt gatccaaacg gtagactatc tactgttggt 361 ggtgtaacga agaaaaataa ccaatcttct gaaactaata cacctttatt tataaaaaaa 421 gtgtatggcg gaaatttaga tgcatcaatt gaatcatttt taattaataa agaagaagtt 481 tcactgaaag aacttgattt caaaattaga caacatttag ttaaaaatta tggtttatat 541 aaaggtacga ctaaatacgg taagatcact ttcaatttga aagatggaga aaagcaagaa 601 attgatttag gtgataaatt gcaattcgag cacatgggcg atgtgttgaa tagtaaggat 661 attcaaaata tagcagtgac tattaatcaa atttaa
```

[SEQ ID NO: 12]-nucleic acid encoding novel SET1 protein [SEQ ID NO: 6]
>set1|GL10 isolate

```
  1 aaagaaaaac aggaacgtgt tcagcacctg tacgacatca aagacctgca 51 ccgttactac tcctccgaat ccttcgaatt ctccaacatc tccggtaaag 101 ttgaaaacta caacggttcc aacgttgttc gtttcaacca ggaaaaacag 151 aaccaccagc tgttcctgct gggtgaagac aaagctaaat acaaacaggg 201 tctgcagggt caggacgttt tcgttgttaa agaactgatc gacccgaacg 251 gtcgtctgtc caccgttggt ggtgttacca aaaaaaacaa ccagtcctcc 301 gaaaccaaca tccacctgct ggttaacaaa ctggacggtg gtaacctgga 351 cgctaccaac gactccttcc tgatcaacaa agaagaagtt tccctgaaag 401 aactggactt caaaatccgt aaacagctgg ttgaaaaata cggtctgtac 451 cagggtacct ccaaatacgg taaaatcacc atcatcctga acggtggtaa 501 aaaacaggaa atcgacctgg gtgacaaact gcagttcgaa cgtatgggtg 551 acgttctgaa ctccaaagac atcaacaaaa tcgaagttac cctgaaacag 601 atctaa
```

[SEQ ID NO: 13]-nucleic acid encoding novel SET1 protein [SEQ ID NO: 7]
>set1|GL1 isolate

```
  1 aaagaaaaac aggaacgtgt tcagcacctg tacgacatca aagacctgca 51 ccgttactac tcctccgaat ccttcgaatt ctccaacatc tccggtaaag 101 ttgaaaacta caacggttcc aacgttgttc gtttcaacca ggaaaaacag 151 aaccaccagc tgttcctgct gggtgaagac aaagctaaat acaaacaggg 201 tctgcagggt caggacgttt tcgttgttaa agaactgatc gacccgaacg 251 gtcgtctgtc caccgttggt ggtgttacca aaaaaaacaa ccagtcctcc 301 gaaaccaaca tccacctgct ggttaacaaa ctggacggtg gtaacctgga 351 cgctaccaac gactccttcc tgatcaacaa agaagaagtt tccctgaaag 401 aactggactt caaaatccgt aaacagctgg ttgaaaaata cggtctgtac
```

```
                              -continued
451 cagggtacct ccaaatacgg taaaatcacc atcatcctga acggtggtaa 501 aaaacaggaa atcgacctgg gtgacaaact gcagttcgaa cgtatgggtg 551 acgttctgaa ctccaaagac atcaacaaaa tcgaagttac cctgaaacag 601 atctaa
```

As noted above, the inventors have identified two novel SET1 proteins represented by the amino acid sequences SEQ ID Nos: 6 and 7, and representative nucleic acids encoding them (SEQ D Nos: 12 and 13). Accordingly, the invention relates to isolated forms of these proteins and nucleic acids encoding them. In this context an "isolated" SET 1 protein or nucleic acid is one which has been identified and separated from at least one contaminant compound (for example a nucleic acid) with which it is associated in its natural state. Accordingly, it will be understood that isolated proteins and nucleic acids are in a form which differs from the form or setting in which they are found in nature. It should be appreciated that 'isolated' does not reflect the extent to which the protein or nucleic acid molecule has been purified.

It should be appreciated that the invention extends to novel SET1 encoding nucleic acids as defined herein (SEQ ID Nos: 12 and 13) which are in association with heterologous nucleic acids, such as regulatory regions and nucleic acids encoding heterologous fusion peptides. The invention also extends to nucleic acid vectors or constructs containing SET1 encoding nucleic acids as defined herein. Such constructs may find use in cloning and expression. The invention also relates to fusion proteins containing the novel SET1 proteins described herein (SEQ ID Nos: 12 and 13).

A SET1 protein or functional equivalent thereof may be made by any number of standard techniques known in the art, having regard to the amino acid and nucleic acid sequences identified herein before. By way of example, they may be isolated from natural sources such as purification from crude culture supernatants of strains of *Staphylococcus aureus* known to produce SET1, produced recombinantly having regard to the genetic code, or produced by chemical protein synthesis. An exemplary protocol for obtaining recombinant SET1 is described herein after under the heading "Examples".

In accordance with a preferred form of the invention, IgA and/or C5 are captured or isolated using affinity chromatography however a skilled person may readily recognise alternative techniques. Generally, an affinity column is prepared combining a SET1 protein or functional equivalent thereof, suitably immobilised on a support resin or matrix.

Any appropriate support resin as known in the art may be used. As it will be appreciated, choice of support resin may depend on the means by which SET1 or a functional equivalent thereof is to be immobilised on it. Preferable support resins include Sepharose such as Sepharose 4B, cyanogen bromide-activated (CNBr-activated) Sepharose, AH-Sepharose 4B and CH-Sepharose 4B, activated CH-Sepharose 4B, Epoxy-activated Sepharose 6B, activated Thiol-Sepharose 4B, Thiopropyl-Sepharose 6B, covalently cross-linked Sepharose (sepharose Cl), and other resins such as nickel chelate resins, cellulose, polyacrylamide, dextran. Such resins may be purchased for example from Pharmacia Biotech. However, a skilled person may produce a resin themselves using methodology standard in the art.

While the inventors have found that it is not necessary to use spacer molecules it should be appreciated that where desirable, and where one is not present on a resin as it may be purchased or manufactured, a spacer molecule may be added to the resin. Such spacer molecule may, in certain circumstances, facilitate the attachment of the ligand (SET1 or a functional equivalent thereof) to the resin, and also facilitate efficient chromatographic isolation of IgA and/or C5. Relevant spacer molecules will readily be appreciated by persons of ordinary skill in the art.

In addition, cross-linking of a support resin, or activation of resins may help facilitate chromatographic separation. Accordingly the invention encompasses this. While support resins which have been cross-linked and/or activated may be readily purchased (for example, Sepharose Cl or CNBr-activated Sepharose) skilled persons will readily appreciate methods for achieving such results themselves.

It will be appreciated that SET1 proteins or their functional equivalents may be chemically modified where necessary and to facilitate attachment to the support resin while not destroying its ability to bind C5 and/or IgA.

Once the support resin is prepared and any modifications made to it and/or a SET1 protein or functional equivalent, the SET1 protein or functional equivalent may be immobilized on the support resin using standard methodology. By way of example, the protein and the resin may simply be mixed for a period of time (by way of example, 2 hours) to allow for attachment of the protein to the resin. Subsequently, any active groups which may remain on the resin may be blocked by mixing with a buffer such as Tris at pH 8.0 for a period of time (for example 2 hours). The protein-resin may then be washed in an appropriate buffer, such as PBS, then suspended in an appropriate buffer and stored. In a preferred from of the invention where a Sepharose resin is used, the protein-resin is stored 1:1 in a PBS/0.025% $NaN_3$ buffer at 4° C. until desired to be used. Further preferred methodology is exemplified herein after under the heading "Examples".

SET1 or a functional equivalent thereof may be combined with the support resin in any desired ratio. In a preferred form of the invention using CNBr-activated Sepharose 4B, SET1 is combined at 7 mg of protein/ml of wet gel Sepharose. This typically results in a concentration of approximately 5 mg protein/ml of Sepharose gel.

Once the affinity matrix or resin is prepared as mentioned herein before it may be formed into a column according to standard techniques readily known in the field. The column may then be washed with an appropriate buffer to prepare it for taking a sample. Such appropriate buffer includes for example PBS, or any other neutral pH buffer containing isotonic concentrations of NaCl. A sample may then be loaded onto the column and allowed to pass over the column. In this step, IgA and/or C5 present in a sample will adsorb to the column resin or matrix.

Appropriate "samples" from which IgA and/or C5 may be captured or isolated include milk, colostrums, serum, tears, saliva, secretions from the gut or any other secretions containing either IgA or complement C5. The sample may be of human, or other animal origin. In one preferred embodiment, the sample is cows milk or collostrum. In another preferred embodiment, the sample is human serum.

Once a sample has passed over the column it will generally be washed with an appropriate buffer to remove unbound or non-specific proteins or other compounds which may have been present in the original sample. Skilled persons will readily appreciate an appropriate buffer suitable for use. However, by way of example, a PBS/300 mM NaCl buffer may be advantageously used.

IgA may be eluted from the column using 100 mM glycine at pH 3.0. In a specific example, 10 column volumes of glycine is used. However, it will be appreciated that this may be varied. The IgA will generally be eluted into any buffer which is adapted to neutralize the elution buffer. The inventors have found that 1M Tris pH 8.0 is appropriate.

C5 may be eluted under similar conditions. The inventors note that C5 elutes at slightly higher pH. Accordingly, a low pH buffer such as 50 mm acetate pH 3.5 may preferably be used for C5.

Following elution or release of IgA and/or C5 from the matrix or column, IgA and/or C5 may be further purified via any number of standard techniques. For example, eluates may be dialysed, or run through an affinity column of the invention again.

It should be appreciated that a chromatographic column in accordance with the invention may be gravity fed, or fed using positive or negative pressure. For example, FPLC and HPLC are applicable to a method of the invention.

Skilled persons will readily appreciate how to implement an HPLC system in relation to the present invention having regard to the information herein and standard methodology documented in the art.

Persons of ordinary skill in the art to which the invention relates will readily appreciate how scale up of bench top columns may be achieved. For example, one may increase volume of the affinity column consistent with the volume of sample to be processed. Commercial scale may be dependent on ensuring that the amount of coupled SET1 saturates the amount of ligand to be bound. Alternatively, large amounts of sample may be processed by repeated processing through a smaller SET1 affinity column. This has the advantage of not requiring so much SET1 but does rely on the reusability of the SET1 for recycling. The inventors have found that SET1 is very stable when used for purification of IgA and/or C5 and can be reused many times without loss of binding activity.

It should be appreciated that an affinity matrix can also be used in batch wise fashion where the solid matrix is added directly to the sample rather than passing the sample through a column. This offers simplicity, but may result in a less clean sample. Such techniques require a step to separate the matrix from the solution or sample. This is normally achieved by gravity sedimentation and decantation of the supernatant followed by washing, or separation of the affinity matrix by low pressure gravity or suction filtration.

The present invention has the advantage of providing a one step system for isolating IgA and/or C5. It should be appreciated that there may be instances where it is desirable to obtain a biological sample that is free from IgA and/or C5. The present invention will allow for substantial removal of these molecules from a sample. The techniques described hereinbefore are suitable for achieving this end. It should be appreciated that where removal of IgA and/or C5 is the objective (as opposed to capture and purification of IgA and/or C5) it would not be necessary to release IgA and/or C5 from any SET1 (or functional equivalent) to which it is bound.

In addition, the inventors demonstration of binding between SET1 and IgA and/or C5, provides a means for detecting the presence, and quantifying the level, of these proteins in a sample. This has diagnostic significance in determining sero-conversion of mucosal immunity (IgA), complement competency (C5) and in detecting abnormalities in these proteins (for example deficiencies, or increased expression, in a subject). Diagnostic methods involving detection and/or quantitation of IgA and/or C5 may find particular use in assessing the immune competence of an individual. For example, reduced salivary IgA levels are believed to be linked to increased susceptibility to infection. This may be of particular benefit to assessing athletes during intensive training regimes, and also assessing the immune status of invalids. Knowledge of immune competence may allow for more informed and individualised approaches to training schedules, nutrition, and medication regimes.

In accordance with the above, the invention also provides methods for detecting the presence, and/or quantifying the level of IgA and/or C5 in a sample. The method will generally comprise the steps: contacting a sample with SET1 or functional equivalent thereof for a period sufficient to allow SET1 or functional equivalent thereof to bind to IgA and/or C5; and, detecting bound SET1 or functional equivalent thereof. The method preferably includes the further step of determining the level of bound SET1 or a functional equivalent thereof. Such a method is applicable to any sample which may contain IgA and/or C5. It is applicable to samples from humans and other animals.

Persons of skill in the art to which the invention relates will appreciate means by which these proteins can be detected and/or quantified. However, by way of example SET1 or a functional equivalent thereof may first be conjugated to peroxidase or alkaline phosphatase by chemical cross-linking using standard methods to produce a staining reagent. Samples can be added to ELISA plates and SET1 or functional equivalent thereof can be added at a fixed concentration to bind to any IgA or C5 bound to the plastic plate surface. Following washing, the amount of SET1 or functional equivalent thereof can be quantified by measuring the amount of peroxidase or alkaline phosphatase bound using established colorimetric methods that result in the production of a coloured compound which can be measured in an ELISA plate reader. The levels of IgA/C5 in the sample can be determined by comparing results against a standard curve of a known sample of either IgA or C5. An alternative example is to utilise a sandwich ELISA employing an anti-SET1 specific antibody. In this case the anti-SET1 antibody is conjugated to either peroxidase or alkaline phosphatase. After the SET1 or functional equivalent thereof has incubated with the sample on the ELISA plate and excess washed away, the anti-SET1 antibody linked to the enzyme is incubated and washed clean.

EXAMPLES

Methods

SET1 Protein Expression and Purification

The SET1 gene was amplified by PCR from the genomic DNA of two local clinical isolates of *Staphylococcus aureus* (designated GL1 and GL10) obtained from Greenlane Hospital (Auckland, New Zealand) using the primer sequences (Forward-BamH1) (Reverse-EcoR1) CG GGATCCAAAGAAAAGCAAGAGAGAG and G GAATTCTTAAATTTGTTTCAAAGTCAC. The PCR fragment was sub-cloned into the expression vector pET32a-3C and expressed in *E. coli* (AD494(DE3)pLysS) as an N-terminal thioredoxin fusion protein. The fusion protein was purified by $Ni^{2+}$ affinity chromatography, cleaved using 3C protease, and subjected to $Ni^{2+}$ affinity chromatography again to separate SET1 from thioredoxin as previously described (11). Purified SET1 was passed through a polymyxin B-agarose column to remove residual *E. coli* endotoxins (Sigma).

Serum and Secreted Samples

Primate sera were provided by kind donation from Auckland Zoo. Fresh sera from rabbit, cow, mice, pigs, horse, sheep and rat was obtained from the Auckland University Animal Research Unit. Human breast milk was provided as a kind donation from a lactating female laboratory technician. Colostrums from cow and sheep were provided by Dr Colin Prosser (AgResearch, New Zealand). Saliva and tears were collected from laboratory individuals and stored under sterile conditions at 4° C.

Bacterial Strains

Staphylococcal strains GL1 and GL10 are part of a large collection of Staphylococcal strains isolated from patients with endocarditis or bacteremia from Green Lane Hospital, Auckland, New Zealand.

Production of Recombinant FcαRI Protein

Soluble FcαRI protein was produced by recombinant baculovirus infection of SF21 insect cells and purified by nickel affinity chromatography as previously described (26).

Coupling of Proteins to Sepharose

Protein in PBS, pH 8.0 was added to CNBr-activated Sepharose 4B (Pharmacia Biotech) at 5-7 mg protein/ml of wet gel sepharose and mixed by rotation at room temperature for 2 hrs. Remaining active groups were blocked with the addition of Tris pH 8.0 to 100 mM and incubating for 2 hrs. The protein sepharose was washed a total of six times in PBS then suspended 1:1 in PBS/0.025% $NaN_3$ and stored at 4° C. Coupling typically resulted in concentrations of approximately 5 mg protein/ml of sepharose gel. Coupled gel was stored in PBS, 0.1% azide at 50% v/v at 4° C.

SET1 Binding Assays

10 μl of SET1-sepharose (50% v/v, equivalent to approximately 50 μl of SET-1) or protein A-sepharose (50% v/v) suspension was added to 10 μl serum or 100 μl secretion respectively and the volume made up to 500 μl with lysis buffer (1% TX-100, 1% bovine hemoglobin, 140 mM NaCl 10 mM Tris.Cl pH 8.0, 0.025% $NaN_3$, 1 mM PMSF, 1 mM iodoacetamide) and incubated with rotation for 1 hour at 4° C. Sepharose without any protein coupled was used as a negative control to determine proteins bound independently of SET1. The samples were washed three times using wash buffer (1% TX-100, 0.1% SDS, 1%-deoxycolate, 500 mM NaCl, 10 mM Tris.Cl pH 8.0), once with TSA (10 mM Tris.Cl pH 8.0, 140 mM NaCl, 0.025% $NaN_3$), and once with 50 mM Tris pH 6.8. Proteins were solubilised by boiling for 2-5 min in 10 μl of SDS-PAGE sample buffer prior to running on a 10 or 12.5% SDS-PAGE gel.

Western Blot Analysis

Proteins bound by SET1-sepharose or protein A-sepharose were resolved on either 10% or 12.5% SDS-PAGE gels under reducing conditions then transferred to a nitrocellulose membrane using a BioRad transblot apparatus (BioRad Laboratories). The nitrocellulose membrane was incubated for 1 hour at room temperature in TTBS (140 mM NaCl, 10 mM Tris.Cl pH 7.6, 0.1% Tween 20) containing 5% (w/v) nonfat milk powder to block non-specific binding. Goat anti-IgA, anti-IgD, anti-IgG, or anti-IgM (Kallestad) was incubated at 1 in 5000 dilution with the membrane fragments for 1 hour at room temperature in TTBS. After 3×15 minute washes in 5 ml TTBS the membrane was incubated with a 1 in 4000 dilution (in TTBS) of biotin labeled rabbit anti-goat IgG (Sigma) for 1 hour at room temperature followed by 3×5 ml washes in TTBS. The membranes were then incubated with a 1 in 4000 dilution of peroxidase labeled avidin (Dako), washed 3 times in TTBS, and analyzed using an ECL Western blotting detection kit (Amersham Pharmacia Biotech) as per the manufacturer instructions.

Flow Cytometric Analysis

Polyclonal human IgA was purified from normal human serum by SET1-sepharose affinity chromatography). 1 mg of IgA was incubated with 1 mg fluorescein isothiocyante (FITC Sigma) for 1 hour at 4° C. then separated from free FITC by chromatography on a 5.0 ml column of Sephadex G25 (Pharmacia). Leukocytes were prepared from whole human blood by first diluting 10-fold with 0.85% ammonium chloride solution to lyse erythrocytes and centrifuging remaining white cells at 2500 rpm×10 min. Leukocytes were suspended at $1\times10^7$ cells/ml in PBS/2% FCS. A 2-fold dilution series from 100 μg to 6.25 μg of SET1 or SEA was prepared in 100 μl PBS/2% FCS. 10 μg polyclonal IgA-FITC was added to each dilution of SET1 and incubated for 15 min at RT in the dark. 50 μl of freshly prepared leukocytes ($5\times10^5$ cells) was added and incubated for 15 min at RT in the dark. Cells were then fixed with the addition of 300 μl 8% formaldehyde and incubating for 3 min at RT in the dark. Cells were washed twice with 1 ml PBS/2% FCS, centrifuged at 400×g for 1 min, and resuspended in 0.5 ml PBS/2% FCS. The cells were analyzed by flow cytometry (FACS Analyser, Becton and Dickinson) with selective gating on the Granulocyte population.

HPLC Affinity Purification of Secretory IgA from Human Breast Milk, Bovine and Ovine Colostrums An HPLC affinity column was generated by coupling 5 mg of purified recombinant SSL7 to 0.7 gm of POROS CNBr activated media (Perceptive Systems, Cambridge Mass.) overnight at room temperature in 50 mM $PO_4$ pH8. The 50 mm×5 cm HPLC column was mounted on a Biocad HPLC (Perceptive systems). Aliquots of human breast milk or bovine or ovine colostrums diluted to 40 mg/ml and filtered were loaded at 10 ml/min in 50 mM $PO_4$ pH6.8. Specifically bound protein was eluted with 2 column volumes of 50 mM glycine pH11.0. Collected peaks were analyzed by SDS PAGE. Bands were excised and subjected to peptide mass fingerprinting.

Biosensor Analysis

SET1 binding to IgA: Purified human serum IgA (Calbiochem) was immobilized on a CM5 carboxyldextran chip using carbodiimide chemistry to a level of ~300 response units (RU) as described previously (26) using a BIAcore2000™ (BIAcore). Purified SET1 in the concentration range 10 to 200 mM was injected over the chip at a flow rate of 30 μl/min. The binding and dissociation kinetics were globally fitted using the BIAevaluation version 2.1 software. The analysis of the equilibrium binding used 120 min injections of SET1 in the concentration range 0.25 to 400 nM SET1. The equilibrium binding response ($R_{eq}$) at 120 min was fitted to the two-site binding model;

$$R_{eq} = B_1 \cdot A/(K_{D1}+A) + B_2 \cdot A/(K_{D2}+A)$$

Where $B_1$, $B_2$, $K_{D1}$, $K_{D2}$ are the respective binding capacities and dissociation constants of the two sites and A is the free analyte concentration.

Equilibrium C5 binding analysis: SET1 (1 μM) was reacted with the immobilized IgA layer (30 μl, flow rate of 10 μl/min) and a subsequent injection (122 μl, flow rate of 1 μl/min) was made of human C5 (Sigma) in the concentration range 2 to 130 nM. For each concentration of C5 the equilibrium binding response to the SET1:IgA was obtained after 120 min as the response above that of the injection of buffer alone. The data was fitted to the single binding site model;

$R_{eq}=B.A/(K_D+[A])$.

The biosensor analysis of SET1 inhibition of IgA binding to FcαRI used rsFcαRI produced by recombinant baculovirus infection of SF21 insect cells and purified by nickel affinity chromatography (26). Briefly rsFcαRI was immobilized on a CM5 carboxyldextran chip for high affinity 2:1 receptor capture of serum IgA described by Wines et al, 2001 (26). Serum IgA (Calbiochem) at 100 nM was injected (20 μl, 10 μl/min) as the analyte and subtraction from a chemically coupled flow cell used to correct for bulk refractive effects. The inhibition of IgA binding was observed by incubating 100 nM IgA with 0-150 nM rSET-1 for 30 min at 25° C., prior to injection on the BIAcore. A binding response report point 1 min after the injection was used to analyze rSET1 inhibition.

Complement Mediated Hemolytic Assay

The assay to detect hemolysis via the alternative complement pathway mediated was followed according to protocols in Handbook of Immunology (27). Serum from normal human individuals was tested for spontaneous hemolytic activity towards allogeneic human red blood cells. Two sera (IB and JL) displayed spontaneous lysis via the alternative activation pathway. Activity was destroyed by heat inactivation (56° C. for 30 minutes) or addition of ethylene diamine tetra acetic acid (EDTA) but not ethylene glycol tetra-acetic acid (EGTA) indicating that lysis was via the alternative pathway. Fresh human erythrocytes were prepared by repeated washing in Gelatin/Veronal buffered saline (GVB=50 mM diethyl barbiturate pH7.4, 1% gelatin, 0.15M NaCl). GVB++ buffer is GVB with $CaCl_2$ and $MgCl_2$ added to 0.06 mM and 0.4 mM respectively. GVBE buffer was GVB with 0.4 mM $MgCl_2$ and 10 mM EGTA. Erythrocytes were standardized at $2\times10^8$ cells/ml in ice cold GVB++. Immediately prior to use, 50 μl of serum diluted 1:2 with GVB++ buffer (25 μl equivalent), was incubated for two hours at 37° C. with varying concentrations of SET1 protein in duplicate in 12×75 mm borosilicate glass tubes. 100 μl human erythrocytes and 50 μl of GVB++ buffer were added and the tubes incubated for 1 hour at 37° C. Total hemolysis was measured by adding 100 μl of water instead of GVB++. To provide a negative control, GVB++ buffer replaced the serum. After 1 hour, 1.2 ml of ice cold 0.15M NaCl was added, tubes were centrifuged at 1250 rpm and hemolysis was measured by the absorbance at 412 nm of the supernatant.

Serum Bactericidal Assay

500 μl aliquots of 1:2 diluted fresh human serum diluted with Hanks balanced salt solution (HBSS) were pre-incubated in duplicate for 30 minutes at 37° C. with varying concentrations of recombinant SSL7 or Staphylococcal Enterotoxin A (SEA) diluted with HBSS in 5 ml borosilicate glass tubes. 10 μl (~$10^7$ cfu) of a fresh mid-log phase ($OD_{620nm}$ 0.15) culture of E. coli K12 (DH5α strain) was washed in HBSS and added to each sample then incubated without mixing for 90 minutes at 37° C. Tubes were placed on ice then 50 μl of appropriate dilutions (up to 1,000,000 fold) were plated onto LB plates and cultured for 24 hrs at 37° C. Surviving colonies were counted the following day.

Peptide Mass Fingerprinting and Protein Identification

Polypeptides were excised from coomassie blue stained SDS PAGE gel, cut into small cubes and subjected to overnight digestion with trypsin (Promega protein sequencing grade 500 IU/mg; Promega, Madison, USA, V511A 11652007) as described previously with minor modifications (29). Digests were dried down in a vacuum dessicator then resuspended in 50 μl of 0.1% acetic acid/0.005% heptafluorobutyric acid in high purity water for injection into an Agilent 1100 series ion-trap mass spectrometer. Peptide mass profiles were analyzed on the MASCOT database (www.matrixscience.com) for protein identification.

Results

SET1 Binds IgA and Complement C5 from Human Serum.

Recombinant SET1 (FIG. 1, lane 3), isolated from the GL1 strain, and recombinant soluble FcαRI CD 89 (FIG. 1, lane 2) were produced to a high level of purity from E. coli and baculovirus infected Sf21 cells respectively (26). Recombinant SET1 was incubated with normal human peripheral blood lymphocytes to test for superantigen activity using a standard 3-day PBL proliferation assay. No proliferative activity was observed over the entire range of SET1 concentrations used (0.1 pg/ml-10 μg/ml) confirming lack of superantigen activity (data not shown). Binding to a soluble form of HLA-DR1 was undetectable by BIAcore analysis (data not shown).

Recombinant SET1 was chemically coupled to sepharose to investigate serum proteins that might bind SET1 directly. Four serum proteins were routinely purified by SET1 from all human sera tested (except for one individual—see below). The two predominant polypeptides of ~60 kD and ~27 kD were observed under reducing conditions but under non-reducing SDS PAGE migrated as a single high MW protein consistent with immunoglobulin heavy and light chain polypeptides (FIG. 2a, lane 3). The identity of the polypeptides excised from the SDS PAGE gel was confirmed by MALDI-TOF mass spectrum fingerprinting (performed by the Australia Proteome Analysis Facility). The 60 kD band was unequivocally identified as human IgA heavy chain while the 27 kD band was confirmed as the Ig light chain. In addition to IgA H and L-chains, two additional polypeptides with molecular weights of 110 kD and 75 kD were also purified by SET1. Although these were less predominant than IgA, their relative abundance to IgA was the same in all individuals tested (except one). Unambiguous identification of these polypeptides was again made by MALDI-TOF mass spectrometry (Australian Proteome Analysis Facility) from bands excised from the SDS PAGE. All samples gave unequivocal matches to human complement component C5 which in serum is composed of two covalently linked chains; C5α chain (115 kD) and C5β chain (75 kD) consistent with the sizes of the bands observed on SDS-PAGE.

Proteomic analysis identified IgA as the predominant species bound by SET1 in serum, but could not exclude other isotypes that might be present in lower abundance. SET1 purified Ig H-chain was compared by SDS PAGE to proteins purified by staphylococcal protein A sepharose (SpA-sepharose) that predominantly binds the IgG isotype but also weakly binds other isotypes in humans. The SpA purified IgG H-chain (~50 kD) (FIG. 2B lane 1) was sufficiently separated in size by SDS PAGE from IgA H-chain (~~60 kD) (FIG. 2B lane 2) to show that very little IgG isotype was bound by SET1. To further confirm this, the SET1 purified proteins were reacted with isotype specific anti-sera by Western blot. Only the anti-IgA antiserum reacted with the protein purified by SET1. Anti-IgG, IgD and IgM were negative (FIG. 2C lane 2). In contrast, all antisera reacted with the SpA purified protein (FIG. 2C lane 1), but the anti-IgG sera was strongest consistent with cross-reactivity of each of the isotype specific anti-sera towards IgG heavy chain. This confirmed that SET1 was selective for the IgA isotype.

SET1 Binds Both Serum and Secreted IgA from Different Species.

Human secretions were tested for secretory IgA binding to SSL7. In these experiments, 10 μl of serum and 100 μl human breast milk, saliva and tears were reacted with 10 μl 50% (v/v) SSL7 sepharose (an equivalent of ~50 μg of coupled SSL7). SSL7 bound IgA from all samples (FIG. 3A). Monomeric IgA along with the C5 α and β-chain polypeptides were bound from the serum sample, while secretory IgA with the additional 75 kD secretory component (SC) were observed in the breast milk, saliva and tear samples. The SC from human breast milk was noticeably smaller than SC from saliva or tears. Nevertheless its identity was confirmed by peptide mass fingerprinting and so the size difference was presumed to be a result of either an alternative proteolytic cleavage of the poly Ig receptor in mammary tissue and/or variable glycosylation differences.

SET1 binding of serum IgA might conceivably be a result of a profound sero-conversion through prior immunization with SET1 producing *S. aureus*. If this were true, then the amount of IgA purified by SET1 from the same volume of sera would be expected to vary between individuals. 10 μl aliquots of serum from 14 individuals were incubated with an equivalent, saturating amount of SET1 sepharose and examined by SDS PAGE. The amount of IgA bound by 13/14 normal volunteers was uniform and consistent suggesting that binding was not unlikely to be via idiotypic regions of the IgA protein. Further studies confirmed that a saturating amount of SET1 extracted all the IgA present in serum with little IgA remaining following a single pass over SET1 sepharose (data not shown). Some individuals (lane 2, 10, 11 and 14 for example) had an additional band at 50 kD that was later confirmed as IgG H-chain (not shown) which provided an excellent contrast between the uniform reactivity towards IgA, and the inconsistent idiotypic reactivity of IgG resulting from variable sero-conversion to SET1. The exception was volunteer 12 (FIG. 3B) who had no detectable SET1 reactive IgA and compensatory levels of anti-SET1 IgG. The absence of IgA in individual 12 was later confirmed to be a result of a genetic IgA deficiency.

Similar amounts of C5 were bound by SET1 from all sera although individuals 5 and 7 showed slightly lower reactivity that might reflect lower serum concentration of C5. C5 binding was clearly apparent in individual 12 confirming that SET1 binding to C5 was independent of IgA binding. This was later confirmed by Biosensor binding analysis (see below).

Analyses were performed on sera from other species and compared to reactivity with staphylococcal protein A (SpA) bound IgG. SET1 strongly bound IgA from human, chimpanzee, baboon and pig sera. Weaker but still detectable binding was observed for horse and rat sera but no detectable binding was seen for cow, sheep, mouse, rabbit, goat IgA. In contrast, SpA bound IgG from the serum from all species (FIG. 3C). SET1 bound polypeptides consistent with complement C5 from human, chimpanzee, baboon, pig, sheep, goat and rabbit serum where SET1 appeared highly selective (FIG. 3C). This experiment took no account of the known differences in serum levels of IgA and C5 across species, but nonetheless provided initial evidence that SSL7 reactivity with both IgA and C5 was not limited to humans. The sizes and SDS migration under reducing and non-reducing conditions of polypeptides bound by SSL7 from other species are consistent with IgA and C5.

Affinity Purification of Secretory IgA from Bovine or Ovine Colostrums and Human Breast Milk Species reactivity in those that showed poor binding of serum IgA was further tested using milk as a source of secretory IgA. Samples of diluted human breast milk (40 mg/ml), diluted bovine or ovine colostrums (also diluted to 40 mg/ml) were passed through a recombinant SET1 HPLC affinity column (FIG. 10). Bound protein was eluted using high pH giving a typical profile shown in FIG. 10. The single peak eluted with high pH was subjected to non-reducing and reducing SDS PAGE (displayed as an insert of FIG. 10). Under non-reducing conditions, a protein with an estimated MW of approximately ~400 kD was routinely observed in the three species corresponding to the predicted size of the IgA dimer (2×170 kD IgA molecules plus a single 75 kD secretory chain along with the 15 kD J (joining) chain). Under reducing conditions this resolved into the secretory chain and the IgA heavy chain (the light chain and J chain were eluted from the bottom of this 7.5% SDS PAGE gel to better separate the high MW polypeptides). In the bovine sample, the SC was slightly lower in molecular weight than the human and ovine SC, presumed to be due to either differences in proteolytic processing or alternatively altered SC glycosylation between these species. The 75 kD and 60 kD polypeptides were confirmed as SC and IgA Heavy chain respectively by peptide mass fingerprinting.

SET1 has Nanomolar Affinity for Both Human IgA and C5.

Biosensor analysis (BIAcore biosensor) confirmed binding to both IgA and C5 and established the affinity of both interactions. Recombinant SET1 protein was reacted with immobilized serum IgA (Calbiochem) and global analysis of the kinetic data fitted well (chi$^2$=0.184) to a model of parallel binding to a heterogeneous ligand with $K_{D1}$=1.0 nM and for the second site $K_{D2}$=330 nM (FIG. 4A). The fit was poor to other models including a single site model. The random coupling of ligand by carbodiimide chemistry to a biosensor chip can result in some orientations of ligand unfavorable for interaction with the analyte. Thus the high affinity site, $K_{D1}$=1.0 nM, most probably reflected the IgA:SET1 interaction. Since serum IgA consists of both IgA1 and IgA2 subclasses this also may contribute to the heterogeneity of the binding behaviour observed. Equilibrium binding analysis, like the kinetic data, best fitted a two-site binding model yielding $K_{D1}$ and $K_{D2}$ values of 1.1±0.2 nM and 80±40 nM respectively for the high and low affinity sites (FIG. 4B). Thus both the kinetic and the equilibrium analysis concur that SET1 displays nanomolar affinity for serum IgA. The binding to recombinant baculovirus produced IgA1-Fc region and to recombinant IgA2 (Gift of Drs Margaret Goodall and Roy Jefferies) confirmed that SET1 binds to both IgA1 and IgA2 isotypes in the Fc region of the molecule (data not shown).

The interaction of SET1 with human C5 was also analyzed using the biosensor. SET1 protein was injected over the immobilized IgA followed by an injection of purified human C5 (Sigma) to demonstrate C5 binding to the SET1 captured on IgA (FIG. 4C). This simultaneous binding of IgA and C5 to SET1 indicates these interactions occur through distinct and functionally separate sites, consistent with the serum binding studies that showed C5 from some species (e.g. rabbit) showed binding to SET1 independent of binding to IgA (FIG. 3C) and volunteer 12 who's complement C5 bound to SET1 in the absence of serum IgA.

The affinity of the SET1 interaction with human C5 was ascertained using IgA to capture SET1, which was then reacted with C5 in the analyte. In this case kinetic analysis was not possible because of the dissociation of the captured SET1 from the IgA layer. However equilibrium analysis was possible with the assumption that the binding of C5 to SET1 did not affect the rate of dissociation of SET1 from the IgA layer. The data obtained fitted well to a single binding site, as often occurs with orientated presentation of ligands to analyte on the biosensor, with a $K_D$=18±1 nM (FIG. 4D).

Allelic Differences in SET1 do not Alter IgA or C5 Binding.

Some SETs such as SET1 exhibit considerable allelic variation among strains of *S. aureus*. To date, 5 alleles of the SET1 gene have been published (MW2, NCTC8325, N315, NCTC6571, Mu50). The amino acid sequences of these published alleles vary by 16% (FIG. 5A). Two further alleles of SET1 were obtained from local clinical isolates called GL1 and GL10. These were cloned and sequenced and compared for their ability to bind human serum IgA. SET1-GL1 and SET1-GL10 differ by 30/210 residues; a variation of 14% yet both bound similar amounts of human IgA from identical volumes of serum from two different people (FIG. 5B). Thus the IgA binding was not significantly altered by the 14% allelic variation observed between the GL1 and GL10 alleles.

SET1 Blocks IgA Binding to Myeloid Cells.

The receptor for IgA is FcαRI (CD89) and is expressed on myeloid cells such as neutrophils, granulocytes, eosinophils, monocytes and macrophages (28). Flow cytometric analysis (FACS) of human granulocytes with FITC-serum polyclonal IgA was performed to determine whether SET1 blocked cell surface binding of IgA to FcαRI (CD89) expressed on myeloid cells such as neutrophils, granulocytes, eosinophils, monocytes and macrophages (28). SET1 was incubated at serial concentrations with a fixed concentration of FITC-IgA (10 μg) prior to incubation with freshly prepared human leukocytes. The superantigen, staphylococcal enterotoxin A (SEA), was used as a negative control. Dose dependent inhibition of IgA binding to cells was observed with SET1 but not with SEA. 90% inhibition was achieved with a 10-fold (w/w) excess of SET1 (100 μg) over FITC-IgA (10 μg). This was equivalent to 70-fold molar excess (FIG. 6). SEA had no inhibitory effect on FITC-IgA binding (FIG. 6). This suggested that SET1 most likely bound to a site on IgA overlapping the FcαRI binding site in the Cα2:Cα3 domains of the IgA H-chain (17).

SET1 Blocks Binding of IgA to Purified FcαRI

To confirm SET1 inhibits of IgA binding to FcαRI, biosensor studies were performed using the FcαRI ectodomains expressed using recombinant baculovirus infected Sf21 insect cells. Purified recombinant soluble FcαRI was immobilized at a level of 500 RU on a BIAcore CM5 biosensor chip. No binding of SET1 (200 nM) to the FcαRI was observed (FIG. 7A). In the absence of SET1 binding of the 100 nM serum IgA to the FcαRI was observed (~220 RU) with kinetics as reported previously (FIG. 7B). Prior incubation of IgA with recombinant SET1 inhibited the binding of IgA to immobilized FcαRI. An approximately equimolar concentration of SET1 (100 nM) to IgA (100 nM) reduced the receptor binding by 70% (62 RU, FIG. 7C). Thus SET1 inhibited IgA binding to FcαRI both in its cell surface form and as soluble proteins with consistent inhibitory kinetics.

SET1 Inhibits Complement-Mediated Lysis and Plasma Bactericidal Activity.

Serum from normal individuals was tested for naturally occurring complement lysis of allogeneic human RBC. Two sera B and JL were found that readily lysed allogeneic RBC in a standard in vitro complement hemolytic assay in the presence of EGTA. IB serum was significantly more hemolytic (100% hemolysis at 2-fold dilution) than JL (40% hemolysis at 2-fold dilution). Hemolysis was negligible following serum heat inactivation (56° C. for 30 minutes) or addition of EDTA but was unaffected by EGTA confirming the activation of the alternate complement pathway (not shown).

Addition of recombinant SET1 to the serum prior to the addition of erythrocytes had a profound inhibitory effect on both IB and JL serum initiated hemolysis (FIG. 8). Maximum inhibition by SET1 was obtained at 1.0 nM (0.63 μg/25 μl serum) for donor IB and 0.26 nM (0.16 μg/25 μl serum) for donor JL. Interestingly, the approximately 3-fold lower amount of SET1 was required to inhibit JL lysis correlated with the 3-fold lower lytic activity of JL serum. As a control, purified recombinant SEA that binds neither serum IgA nor complement C5, displayed no inhibition even at the highest concentration tested. The slightly lower maximum lysis of IB serum between the SET1 inhibition experiment (~80%) and the SEA inhibition experiment (~50%) was most likely due to aging of the serum as these two assays were performed two days apart.

SSL7 Enhances Survival of Bacteria in Serums

SET1 was tested for its ability to provide protection to a bacterium that was sensitive to plasma bactericidal killing. Recombinant SET1 was incubated with fresh human serum over a range of concentrations prior to the addition of ~$10^7$ *E. coli* K12 bacteria, a bacterium which does not survive in human blood, as it is susceptible to complement lysis. In the absence of SET1, no cells survived after a 90-minute incubation of $10^7$ bacteria at 37° C. with 500 μl fresh serum diluted 1:2 in HBSS. Addition of recombinant SET1 at concentrations above 0.26 nM (7 μg/ml) profoundly inhibited serum anti-microbial activity and increased the number of surviving *E. coli* cells to a maximum level of 14% at 2.1 nM (50 μg/ml) (FIG. 9). The control recombinant SEA had no effect on lysis even at the highest concentration used (50 μg/ml).

Discussion

Herein describes the first reported function(s) for a member of the eleven gene cluster of SETs (or SSLs) located on the staphylococcal pathogenicity island, SaPIn2 ((3), (10)). SET1 (or SSL7) selectively bound both purified IgA and complement C5 and inhibited complement and IgA:FcαRI binding—two important components of the host protective immune mechanisms against *S. aureus*. SET1 also inhibited the bactericidal activity of plasma against a sensitive organism (in this case *E. coli*) at concentrations consistent with the approximate serum concentration of complement C5. The structural homology between SETs and the superantigens argues a close evolutionary relationship between these protein families, but this study reveals that the prototypical SET family member, SET1, has unique functions not shared with the superantigen family. These functions, leukocyte IgA receptor inhibition and complement inhibition, mediated through binding IgA and C5 respectively, reflect specialization of this superantigen-like class in microbial defense. A number of other recombinant SETs have been tested for IgA binding and/or complement inhibition but so far, only SET1 displays this capacity.

SET1 bound with high affinity to IgA and inhibited IgA:FcαRI complex formation most probably through competition for binding at the IgA-Fc Cα2-Cα3 interface where the first ectodomain of FcαRI binds (17, 20-22, 26). SET1 inhibition of IgA binding to FcαRI was seen in a biosensor assay configured for high affinity bivalent capture of IgA (17, 26) and 70% inhibition was achieved by 1:1 addition of 100 nM SET1 with 100 nM IgA. The high affinity ($K_D$~1 nM) binding of SET1 to each IgA would result in about ¾s of the IgA molecules having one or both heavy chains occupied by SET1 and so unavailable for bivalent capture by immobilized rsFcαRI. Moreover, SET1 bound equally sIgA and momomeric IgA from serum, indicating that the SET1 could affect immune evasion both in humoral and mucosal environments. Competition of SET1 and rsFcαRI for binding to IgA suggests that the most likely scenario is two SET1 binding sites per IgA-Fc. Furthermore SET1 binding of secretory IgA suggests that either the SET1 and SC binding site are completely separate, or the single SC in the sIgA incompletely occupies the SET1 binding sites.

SET1 is the first example of a staphylococcal immunoglobulin binding protein that selectively targets IgA and provides a mode of defense not previously described for this pathogen. Staphylococcal protein A (SpA) is the prototypic staphylococcal immunoglobulin binding protein. It is a surface bound protein that binds predominantly to the Fc region of IgG through its repeat domains. This direct coating of the bacteria in IgG is thought to prevent IgG function by orientating the Fc in such a manner so that it cannot activate FcγRI or complement. In contrast to SpA, SET1 is a secreted protein apparently without multiple repeated binding domains that selectively targets an isotype not previously considered important in defense against staphylococci.

The ability of SET1 to block IgA binding to its FcαRI (CD89) suggests a possible role in inhibiting Fc receptor-mediated leukocyte activation that leads to respiratory burst, cytokine release and phagocytosis. The human pathogens *Streptococcus pyogenes* and group B *streptococcus* also produce IgA binding proteins suggesting there is a selective advantage for these microbes to evade IgA-mediated defense mechanisms. These proteins, Arp4 and Sir22, are M proteins from *S. pyogenes* and the unrelated β protein from group B *streptococcus* all bind IgA-Fc at the same site as the leukocyte receptor FcαRI, and like SET1, also block IgA binding to FcαRI bearing granulocytes (26).

The binding and inhibition of complement C5 by SET1 is novel. The site of binding on C5 remains to be identified. One possible site would be the C3-convertase cleavage site preventing the formation of C5a anaphylatoxin and C5b initiator of MAC (preliminary evidence of binding of SET1 to activated C5 suggests however that it binds to the C5 beta chain—not shown). Here, SET1 was shown to inhibit complement-mediated hemolysis and enhance bacterial survival of *E. coli* at concentrations similar to the concentration of C5 in serum. The inhibition of complement C5 cleavage to C5a anaphylatoxin would be a more important mechanism to the survival of *S. aureus*. C5a initiates inflammatory responses, leukocyte recruitment and phagocytosis, which are all important for the destruction of gram-positive organisms.

SET1 enhanced microbial survival, inhibiting plasma killing of *E. coli* an organism that is sensitive to human plasma *E. coli* was used instead of *S. aureus*, because the latter organism is likely to produce its own endogenous SET1 and is thus capable of better surviving in plasma without additional SET1. Inhibitory activity of this cytolytic activity was first observed at concentrations above 0.3 nM and increased to a maximum of approximately 1.7 nM. This concentration is most consistent with the approximated concentration of C5 in serum (0.4 nM). Inhibition was not profound with only a maximum of 0.03% surviving colonies (3000 colonies from an initial $10^7$ inoculum). This would suggest *E. coli* is killed by a number of mechanisms, only one of which (C5 mediated complement) is inhibited by SET1. Notably, the plasma used was not depleted of phagocytic cells that might represent an additional killing mechanism of *E. coli* not inhibited by SET1. SET1 likely represents only a component of a defense mechanism involving multiple factors including other members of the SET (or SSL) cluster.

The results described herein indicate SET1 affinity chromatography may offer a simple single step method for the purification of IgA and C5, which have both traditionally been laborious molecules to isolate using classical methods.

The invention has been described herein with reference to certain preferred embodiments, in order to enable the reader to practice the invention without undue experimentation. Those skilled in the art will appreciate that the invention is susceptible to variations and modifications other than those specifically described. It is to be understood that the invention includes all such variations and modifications. Furthermore, titles, headings, or the like are provided to enhance the reader's comprehension of this document, and should not be read as limiting the scope of the present invention.

The entire disclosures of all applications, patents and publications, cited above and below, if any, are hereby incorporated by reference.

The reference to any prior art in this specification is not, and should not be taken as, an acknowledgment, or any form of suggestion, that that prior art forms part of the common general knowledge in the field of endeavour to which the invention relates in any country.

Throughout this specification, and any claims which follow, unless the context requires otherwise, the words "comprise", "comprising" and the like, are to be construed in an inclusive sense as opposed to an exclusive sense, that is to say, in the sense of "including, but not limited to".

REFERENCES

1. Van Belkum, A., M. Kools-Sijmons, and H. Verbrugh. 2002. Attachment of *Staphylococcus aureus* to eukaryotic cells and experimental pitfalls in staphylococcal adherence assays: a critical appraisal. *J Microbiol Methods* 48:19-42.
2. Novick, R. P., P. Schlievert, and A. Ruzin. 2001. Pathogenicity and resistance islands of staphylococci. [Review][57 refs]. *Microbes & Infection* 3:585-594.
3. Kuroda, M., T. Ohta, I. Uchiyama, T. Baba, H. Yuzawa, 1. Kobayashi, L. Cui, A. Oguchi, K. Aoki, Y. Nagai, J. Lian, T. Ito, M. Kanamori, H. Matsumaru, A. Maruyama, H. Murakami, A. Hosoyama, Y. Mizutani-Ui, N. K. Takahashi, T. Sawano, R. Inoue, C. Kaito, K. Sekimizu, H. Hirakawa, S. Kuhara, S. Goto, J. Yabuzaki, M. Kanehisa, A Yamashita, K. Oshima, K. Furuya, C. Yoshino, T. Shiba, M. Hattori, N. Ogasawara, H. Hayashi, and K. Hiramatsu. 2001. Whole genome sequencing of meticillin-resistant *Staphylococcus aureus*. *Lancet* 357:1225-1240.
4. Novick, R. P. 2003. Mobile genetic elements and bacterial toxinoses: the superantigen-encoding pathogenicity islands of *Staphylococcus aureus*. *Plasmid* 49:93-105.
5. Fraser, J., V. Arcus, P. Kong, E. Baker, and T, Proft. 2000. Superantigens—powerful modifiers of the immune system. *Mol Med Today* 6:125-132.
6. Arcus, V. L., T. Proft, J. A. Sigrell, H. M. Baker, J. D. Fraser, and E. N. Baker. 2000. Conservation and variation in superantigen structure and activity highlighted by the three-dimensional structures of two new superantigens from *Streptococcus pyogenes*. *Journal of Molecular Biology* 299:157-168.
7. Arcus, V. 2002. OB-fold domains: a snapshot of the evolution of sequence, structure and function. *Current Opinion in Structural Biology* 12:794-801.
8. Williams, R. J., J. M. Ward, B. Henderson, S. Poole, B. P. O'Hara, M. Wilson, and S. P. Nair. 2000. Identification of a novel gene cluster encoding staphylococcal exotoxin-like proteins: characterization of the prototypic gene and its protein product, SSL7. *Infection & Immunity.* 68:4407-4415.
9. Kim, J., R. Urban, J. L. Strominger, and D. Wiley. 1994. Toxic Shock Syndrome Toxin-1 Complexed with a Major Histocompatibility Molecule HLA-DR1. *Science* 266:1870-1874.
10. Baba, T., F. Takeuchi, M. Kuroda, H. Yuzawa, K. Aoki, A. Oguchi, Y. Nagai, N. Iwama, K. Asano, T. Naimi, H. Kuroda, L. Cui, K. Yamamoto, and K. Hiramatsu. 2002. Genome and virulence determinants of high virulence community-acquired MRSA. *Lancet* 359:1819-1827.
11. Arcus, V. L., R. Langley, T. Proft, J. D. Fraser, and E. N. Baker. 2002. The Three-dimensional Structure of a Superantigen-like Protein, SSL3, from a Pathogenicity Island of the *Staphylococcus aureus* Genome. *J Biol Chem* 277:32274-32281.
12. Fitzgerald, J. R., D. E. Sturdevant, S. M. Mackie, S. R Gill, and J. M. Musser. 2001. Evolutionary genomics of *Staphylococcus aureus*: insights into the origin of methicillin-resistant strains and the toxic shock syndrome epidemic. *Proc Natl Acad Sci USA* 98:8821-8826.
13. Kerr, M. A. 1990. The structure and function of human IgA. *Biochemical Journal.* 271:285-296.
14. Van Spriel, A. B., J. H. Leusen, H. Vile, and J. G. Van De Winkel. 2002. Mac-1 (CD11b/CD18) as accessory molecule for Fc alpha R(CD89) binding of IgA. *J Immunol* 169:3831-3836.
15. van Egmond, M., C. A. Damen, A. B. van Spriel, G. Vidarsson, E. van Garderen, and J. G. J. van de Winkel. 2001. IgA and the IgA Fc receptor. *Trends in Immunology* 22:205-211.
16. Corthesy, B. 2002. Recombinant immunoglobulin A: powerful tools for fundamental and applied research. *Trends in Biotechnology* 20:65-71.
17. Herr, A. B., E. R. Ballister, and P. J. Bjorkman. 2003. Insights into IgA-mediated immune responses from the crystal structures of human FcaII and its complex with IgA1-Fc. *Nature* 423:614-620.
18. Morton, H. C., and P. Brandtzaeg. 2001. CD89: the human myeloid IgA Fc receptor. *Archivum Immunologiae et Therapiae Experimentalis.* 49:217-229.
19. van Egmond, M., E. van Garderen, A. B. van Spriel, C. A. Damen, E. S. van Amersfoort, G. van Zandbergen, J. van Hattum, J. Kuiper, and J. G. van de Winkel. 2000. FcalphaRI-positive liver Kupffer cells: reappraisal of the function of immunoglobulin A in immunity. *Nature Medicine.* 6:680-685.
20. Pleass, R., J. Dunlop, C. Anderson, and J. Woof. 1999. Identification of residues in the CH2/CH3 domain interface of IgA essential for interaction with the human fcalpha receptor (FcalphaR) CD89. *Journal of Biological Chemistry* 274:23508-23514.
21. Carayannopoulos, L., J. Hexham, and J. Capra. 1996. Localization of the binding site for the monocyte immunoglobulin (Ig) A-Fc receptor (CD89) to the domain boundary between Calpha2 and Calpha3 in human IgA1. *Journal of Experimental Medicine.*
22. Wines, B., M. Hulett, G. Jamieson, H. Trist, J. Spratt, and P. Hogarth. 1999. Identification of residues in the first domain of human Fc alpha receptor essential for interaction with IgA. *Journal of Immunology* 162:2146-2153.
23. Nilsson, U. R., R. J. Mandle, Jr., and J. A. McConnell-Mapes. 1975. Human C3 and C5: subunit structure and modifications by trypsin and C42-C423. *J Immunol* 114:815-822.
24. Tack, B. F., S. C. Morris, and J. W. Prahl. 1979. Fifth component of human complement: purification from plasma and polypeptide chain structure. *Biochemistry* 18:1490-1497.
25. Gerard, N. P., and C. Gerard. 1991. The chemotactic receptor for human C5a anaphylatoxin. *Nature* 349:614-617.
26. Wines, B., C. Sardjono, H. Trist, C. Lay, and P. Hogarth. 2001. The Interaction of FcalphaRI with IgA and Its Implications for Ligand Binding by Immunoreceptors of the Leukocyte Receptor Cluster. *Journal of Immunology:* 1781-1789.
27. Shevach, E. N. 1994. Complement. In Current Protocols in Immunology. W. Strober, editor. John Wiley and Sons Ltd, New York. 13.10.11.
28. Morton, H. C., M. van Egmond, and J. G. van de Winkel. 1996. Structure and function of human IgA Fc receptors (Fc alpha R). *Critical Reviews in Immunology.* 16:423-440.
29. Shevchenko, A., M. Wilm, O. Vorm, and M. Mann. 1996. Mass spectrometric sequencing of proteins silver-stained polyacrylamide gels. *Anal Chem* 68:850.

The invention claimed is:

1. A method of isolating IgA present in a sample, the method comprising at least the steps of:
   bringing a SET1 polypeptide in contact with the sample for a period sufficient to allow the SET1 polypeptide to bind to IgA to form a complex;
   separating the complex; and,
   releasing IgA from the complex;
   wherein the SET1 polypeptide comprises (a) an amino acid sequence having at least 80% similarity to SEQ ID NO:1, or (b) a fragment of the amino acid sequence that lacks only a signal peptide sequence as compared to the amino acid sequence.

2. A method for isolating IgA from a sample, the method comprising at least the steps of:
   providing a matrix to which a SET1 polypeptide is bound;
   providing a sample;
   bringing said matrix and said sample into contact for a period sufficient to allow the SET1 polypeptide to bind to IgA present in the sample; and,
   releasing IgA from the matrix,
   wherein the SET1 polypeptide comprises (a) an amino acid sequence having at least 80% similarity to SEQ ID NO:1, or (b) a fragment of the amino acid sequence that lacks only a signal peptide sequence as compared to the amino acid sequence.

3. A method as claimed in claim 2 wherein the method further comprises the step of collecting the IgA released.

4. A method as claimed in claim 2 wherein the matrix is in the form of a column over which the sample is passed.

5. A method as claimed in claim 2 wherein the method further comprises the step of washing contaminants present in the sample from the matrix prior to release of IgA.

6. A method as claimed in claim 2 wherein the matrix is Sepharose.

7. A method as claimed in claim 2 wherein the sample is milk.

8. A method as claimed in claim 2 wherein the sample is colostrum.

9. A method as claimed in claim 2 wherein the sample is serum.

10. A method as claimed in claim 2 wherein the method further comprises the step of determining the quantity of IgA present in the sample.

11. A method as claimed in claim 2 wherein IgA is released from the matrix using a 100 mM glycine buffer at pH 3.0.

12. A method of detecting IgA in a sample, the method comprising at least the steps of:
contacting a sample with a SET1 polypeptide for a period sufficient to allow the SET1 polypeptide to bind to IgA; and,
detecting bound SET1 polypeptide, wherein the SET1 polypeptide comprises (a) an amino acid sequence having at least 80% similarity to SEQ ID NO:1, or (b) a fragment of the amino acid sequence that lacks only a signal peptide sequence as compared to the amino acid sequence.

13. A method as claimed in claim 12 wherein the method further includes the step of determining or quantifying the level of the bound SET1 polypeptide.

14. A method as claimed in claim 12 wherein the method is conducted for the purpose of diagnosing IgA abnormality in a subject.

15. A method as claimed in claim 12 wherein the subject is a mammal.

16. A method as claimed in claim 15 wherein the mammal is a human.

17. A method of removing IgA from a sample, the method comprising at least the steps of:
bringing a SET1 polypeptide in contact with the sample for a period sufficient to allow the SET1 polypeptide to bind to IgA to form a complex; and,
separating the complex from the sample,
wherein the SET1 polypeptide comprises (a) an amino acid sequence having at least 80% similarity to SEQ ID NO:1, or (b) a fragment of the amino acid sequence that lacks only a signal peptide sequence as compared to the amino acid sequence.

18. The method as claimed in claim 1, wherein the SET1 polypeptide comprises the fragment, which is a mature SET1 having the amino acid sequence selected from the group consisting of SEQ ID NO:6, SEQ ID NO:7, and SEQ ID NOs:14-18.

19. The method as claimed in claim 18, wherein the SET1 polypeptide is a fusion protein containing the mature SET1.

20. The method as claimed in claim 1, wherein the SET polypeptide comprises a precursor SET1 having the amino acid sequence selected from the group consisting of SEQ ID NOs:1 and 3-5.

21. The method as claimed in claim 20, wherein the SET polypeptide is a fusion protein containing the precursor SET1.

22. The method as claimed in claim 2, wherein the SET1 polypeptide comprises the fragment, which is a mature SET1 having the amino acid sequence selected from the group consisting of SEQ ID NO:6, SEQ ID NO:7, and SEQ ID NOs:14-18.

23. The method as claimed in claim 22, wherein the SET1 polypeptide is a fusion protein containing the mature SET1.

24. The method as claimed in claim 2, wherein the SET polypeptide comprises a precursor SET1 having the amino acid sequence selected from the group consisting of SEQ ID NOs:1 and 3-5.

25. The method as claimed in claim 24, wherein the SET polypeptide is a fusion protein containing the precursor SET1 protein.

26. The method as claimed in claim 12, wherein the SET1 polypeptide comprises the fragment, which is a mature SET1 having the amino acid sequence selected from the group consisting of SEQ ID NO:6, SEQ ID NO:7, and SEQ ID NOs:14-18.

27. The method as claimed in claim 26, wherein the SET1 polypeptide is a fusion protein containing the mature SET1.

28. The method as claimed in claim 12, wherein the SET polypeptide comprises a precursor SET1 having the amino acid sequence selected from the group consisting of SEQ ID NOs:1 and 3-5.

29. The method as claimed in claim 28, wherein the SET polypeptide is a fusion protein containing the precursor SET1.

30. The method as claimed in claim 17, wherein the SET1 polypeptide comprises the fragment, which is a mature SET1 having the amino acid sequence selected from the group consisting of SEQ ID NO:6, SEQ ID NO:7, and SEQ ID NOs:14-18.

31. The method as claimed in claim 30, wherein the SET1 polypeptide is a fusion protein containing the mature SET1.

32. The method as claimed in claim 17, wherein the SET polypeptide comprises a precursor SET1 having the amino acid sequence selected from the group consisting of SEQ ID NOs:1 and 3-5.

33. The method as claimed in claim 32, wherein the SET polypeptide is a fusion protein containing the precursor SET1.

* * * * *